(12) United States Patent
Evans et al.

(10) Patent No.: US 12,274,639 B2
(45) Date of Patent: Apr. 15, 2025

(54) METHOD OF FORMING AN OSTOMY POUCH

(71) Applicant: ConvaTec Limited, Flintshire (GB)

(72) Inventors: Kevin Evans, Flintshire (GB); Mark Jones, Flintshire (GB)

(73) Assignee: CONVATEC LIMITED, Flintshire (GB)

( * ) Notice: Subject to any disclaimer, the term of this patent is extended or adjusted under 35 U.S.C. 154(b) by 0 days.

(21) Appl. No.: 18/675,925

(22) Filed: May 28, 2024

(65) Prior Publication Data

US 2024/0307212 A1    Sep. 19, 2024

Related U.S. Application Data

(63) Continuation of application No. PCT/GB2022/053020, filed on Nov. 29, 2022.

(30) Foreign Application Priority Data

Nov. 30, 2021    (GB) ..................................... 2117252

(51) Int. Cl.
    *A61F 5/445*    (2006.01)
    *A61F 5/44*     (2006.01)
    *B32B 37/12*    (2006.01)

(52) U.S. Cl.
    CPC ............ *A61F 5/445* (2013.01); *A61F 5/4404* (2013.01); *B32B 37/12* (2013.01); *B32B 37/1207* (2013.01)

(58) Field of Classification Search
    CPC .. A61F 5/445; A61F 5/4404; B29C 2793/009; B29C 65/18; B29C 66/1122; B29C 66/472; B29C 66/71; B29C 66/712; B29C 66/7292; B29C 66/7392; B29C 66/81463; B29C 66/919; B29C 66/929; B29C 66/949; B29D 22/003; B29K 2023/083; B29K 2067/00;
    (Continued)

(56) References Cited

U.S. PATENT DOCUMENTS

| 11,950,984 B2 | 4/2024 | Pratt et al. |
| 11,957,545 B2 | 4/2024 | Hunt et al. |

(Continued)

FOREIGN PATENT DOCUMENTS

| EP | 2268239 A1 | 1/2011 |
| EP | 4353271 A1 | 4/2024 |

(Continued)

OTHER PUBLICATIONS

International Preliminary Report on Patentability for PCT/GB2022/053020; Completed Dec. 2, 2024; 10 pages.

*Primary Examiner* — Sonya M Sengupta
(74) *Attorney, Agent, or Firm* — TAFT STETTINIUS HOLLISTER LLP; Ryan O. White; Derek B. Lavender

(57) ABSTRACT

A method of forming an ostomy pouch comprising: providing a film to form a first cavity wall and a second cavity wall; providing a comfort material to form a comfort layer; wherein the comfort material is a woven fabric material with a hot melt adhesive coating thereon; joining the first cavity wall to the second cavity wall at a first temperature and a first pressure for a first time period; and subsequently joining a comfort layer to at least one of the first and second cavity walls at a second temperature and a second pressure for a second time period.

20 Claims, 10 Drawing Sheets

(58) Field of Classification Search
CPC ........ B29K 2105/0845; B29K 2313/02; B29K 2713/02; B29L 2031/7148; B32B 37/12; B32B 37/1207
See application file for complete search history.

(56) References Cited

U.S. PATENT DOCUMENTS

| | | |
|---|---|---|
| 11,964,095 B2 | 4/2024 | Robinson et al. |
| 11,969,538 B2 | 4/2024 | Quintanar |
| 11,992,392 B2 | 5/2024 | Earl et al. |
| 12,016,993 B2 | 6/2024 | Johnson et al. |
| 2014/0309604 A1 | 10/2014 | Paratore |
| 2024/0139035 A1 | 5/2024 | Collinson et al. |
| 2024/0148560 A1 | 5/2024 | Coulthard et al. |
| 2024/0156645 A1 | 5/2024 | Braga et al. |
| 2024/0189492 A1 | 6/2024 | Gowans et al. |
| 2024/0197538 A1 | 6/2024 | Cole et al. |
| 2024/0307212 A1 * | 9/2024 | Evans ................ B32B 37/1207 |

FOREIGN PATENT DOCUMENTS

| | | |
|---|---|---|
| EP | 3292878 B1 | 5/2024 |
| EP | 4025164 B1 | 5/2024 |
| EP | 4359028 A1 | 5/2024 |
| GB | 2606959 B | 6/2024 |
| WO | 2021064409 A1 | 4/2021 |

* cited by examiner

METHOD OF FORMING AN OSTOMY POUCH

TECHNICAL FIELD OF THE INVENTION

The present invention relates to a method of forming an ostomy pouch for managing effluent from a stoma.

BACKGROUND TO THE INVENTION

There are many forms of ostomy pouch, for example, open and closed, one-piece or two-piece. Pouches may have various shapes and various components. Typically, they comprise a cavity formed of a (normally plastic) film, frequently formed by two layers, front and rear, welded together at their periphery, with the rear layer of film (closest to the ostomate's body in use) including an aperture through which effluent can enter the pouch.

For the comfort of the ostomate, a "comfort layer" can be provided, overlying the rear film layer, and normally the front film layer too. The comfort layer is made of a material that is more comfortable against the skin than the film. Normally, the comfort layer is a non-woven material—non-woven materials are chosen for features such as cost and ease of assembly, for example because they can be easily attached to the film layers of the pouch by the same welding process that bonds the film layers to one another at their periphery.

More recently, however, as part of efforts to make ostomy pouches seem less "medical", and more attractive to users, woven materials have been introduced as the comfort material of the Salts® Confidence BE® product, with the product being described in advertising material as "stylish". A woven material is more likely to be mistaken by others noticing the pouch as an undergarment, rather than as a medical appliance.

Whilst this is considered desirable, the production of an ostomy pouch with a woven comfort layer is considered to be complex. The Salts® Confidence BE® product appears to include a complete layer of specially chosen film material adjacent the woven layer. Thus, in one example, moving from the ostomate out, there is: a rear woven comfort layer; an opaque rear wall defining one side of a cavity; a clear front wall defining the other side of the cavity; an opaque intervening wall; and a front woven comfort layer. The front comfort layer is provided in two parts, top and bottom separated by a split and overlapping in the region of the split, so that the comfort layer can be pulled apart at the split to inspect the contents through the clear wall. The intervening layer is similarly provided in two parts, bonded to the periphery of the two parts of the comfort layer. In this example, the intervening wall appears to avoid fraying of the edges of the comfort layer; avoid visibility of the contents; or aid in the processability of the (somewhat stretchy) fabric that it is adhered to.

This additional wall has a number of drawbacks for the pouch including: increased complexity of construction, increased cost, increased bulk, and increased noise in use as there is yet another layer which can rustle making the pouch less discreet.

It is an object of embodiments of the present invention to at least partially overcome or alleviate the above problems.

SUMMARY OF THE INVENTION

In this specification, the term "stomal output" refers to any gases or fluids or solids produced by an ostomate that may be secreted from the stoma or that exit the stoma. The stomal output may comprise stomal gas, stomal liquid and stomal solids.

In this specification, the term "stoma" refers to an opening in the body. Generally, the stoma is a surgical opening in the torso of the body. In some instances, the term "stoma" also refers to internal tissue, organs, or portions thereof that are exposed by the opening. By way of non-limiting example, internal tissue may be selected from colon, ileum, small intestine, large intestine, jejunum, and duodenum, and combinations thereof. The internal tissue may be an end or a loop of a small or large intestine.

In this specification, the term "ostomate" refers to a subject that may have use of the ostomy pouch disclosed herein. While ostomate usually refers to a subject with a surgical opening, as used herein, "ostomate" may refer to a subject who has a stoma, regardless of whether the stoma was created by surgery or other means.

The term "user" may refer to an ostomate, or to another person assisting the ostomate, for example, with emptying of the stomal output from the cavity.

In this specification, the ostomy pouches disclosed herein may, for example, be used for managing a stoma created by an esophagostomy, a gastrostomy, a cholecystostomy, a choledochostomy, a cecostomy, a colostomy, a duodenostomy, an ileostomy, a jejunostomy, an appendicostomy, a tracheostomy, an urostomy, a nephrostomy, an ureterostomy, or a vesicostomy. The ostomy pouches disclosed herein may be used with additional devices including, but not limited to, a shunt, a catheter, a plug, or a faecal management system.

Beneficially, the ostomy pouches of the present disclosure may permit an ostomate to increase the period of use of each ostomy pouch compared to prior art pouches. This may be achieved, for example, by providing an increased cavity volume for the ostomy pouch while maintaining ostomate discretion and comfort. Additionally, or alternatively, this may also be achieved by providing means for draining the cavity of stomal output reliably and hygienically so as to increase an ostomate's confidence in reusing the ostomy pouch compared to some prior art pouches. Since the ostomate may be inclined to use each ostomy pouch of the present disclosure for longer, the total number of ostomy pouches used by the ostomate in a given time period may be reduced. This may produce an environmental benefit in reducing the amount of environmental waste produced.

In this specification locations and orientations of features may be described with reference to the ostomy pouch being "in use", "orientated as it would be "in use" or similar. Such terms refer to the intended orientation of the ostomy pouch when it is adhered to a body of an ostomate with the ostomate in a standing position, irrespective of whether the ostomy pouch is currently performing such a use or the actual position of the ostomate. The terms "upper" and "lower" and related terms refer to the relative position of a part or portion of the ostomy pouch when orientated as it would be in use. For example, a section of the ostomy pouch may be referred to as an "upper" section of the ostomy pouch. In such an example, said section will be intended to be the uppermost section (in the vertical direction) of the ostomy pouch when attached to the body of a standing ostomate. However, the reader skilled in the art will appreciate that before attachment to the ostomate said section may not always be the uppermost section and in addition when attached the section may not always be the uppermost section if the ostomate adopts a non-standing position, for example lying down.

The terms "left-hand" and "right-hand" and related terms refer to the ostomy pouch when viewed from the rear (for example, as shown in FIG. 1). Thus, as an illustrative example, a "left-hand" edge of the ostomy pouch will be towards a left-hand side of the ostomate in the situation where the ostomy pouch is attached to the front torso of the ostomate.

The terms "concave" and "convex" and related terms refer to shaping of features of the ostomy pouch when viewed from an exterior of the ostomy pouch. Thus, as an illustrative example, an ostomy wafer of circular shape would be considered to have a convexly shaped peripheral edge.

In this specification the terms "front" and "rear" refer to the relative position of a part or portion of the ostomy pouch with reference to the body of an ostomate when the ostomy pouch is attached to the body. "Rear" refers to a position relatively closer to the body of the ostomate than a comparative position that is "front". "Front" refers to a position relatively further away from the body of the ostomate than a comparative position that is "rear".

In this specification the term "smoothly blends" and related terms refers to the smooth merging of two edges, lines, or contours without abrupt changes in contour.

In this specification the term "peripheral region" refers to a portion situated on or towards an edge of the item being referred to.

The term "turned up" used herein may include folding or rolling of the components.

Ostomy pouches are commonly attached to the body by means of an ostomy wafer which includes an adhesive layer or layers. The ostomy wafer typically has an opening for the stoma sometimes referred to as a starter hole which may be cut to a required size by a user before attachment. The ostomy wafer typically comprises an adhesive layer on a body-facing side for adhering the ostomy wafer to the body of the ostomate. Typically, a release liner covers a body-facing side of the ostomy wafer that is removed by the user prior to fitting to the skin. In this specification, the term "ostomy wafer" may be used interchangeably with the terms "adapter," "wafer," "baseplate", or "layered adhesive wafer." In this specification, the term "ostomy wafer" includes ostomy wafers for a "two-piece pouch" and for a "one-piece pouch".

In this specification a "two-piece pouch" refers to a pouch where the ostomy wafer forms part of a separate body fitment component that is attached by a releasable coupling to the remainder of a pouch. A two-piece pouch permits the body fitment component to be separated from the pouch without damage, so that at least one of the parts continues to be functionally usable. For example, the body fitment component may remain in place on the body of the ostomate.

In this specification a "one-piece pouch" refers to a pouch where the ostomy wafer is permanently attached to the pouch, to the extent that the ostomy wafer cannot easily be separated without risk of damaging the pouch. A one-piece pouch is intended to be used as an integral unit.

Ostomy pouches are commonly configured as closed pouches or open pouches. In this specification a "closed pouch" refers to an pouch where it is not intended that stomal output is drained from the cavity. Thus, a closed pouch may typically be configured as a one-use, disposable, and non-reusable pouch. In this specification an "open pouch" refers to an pouch where it is intended that stomal output is drained from the cavity. Thus, an open pouch may be configured as a reusable pouch, such that it can be reused and emptied multiple times whilst attached to the body, although this is not essential. In an open pouch the stomal output may be drained intermittently as instigated by an action of the ostomate or may be drained intermittently or continuously due to the cavity being fluidly connected to a drain, for example a night drain line.

A broad aspect of the invention concerns joining a first cavity wall to a second cavity wall at a first temperature and a first pressure for a first time period; and subsequently, joining a comfort layer to at least one of the first and second cavity walls at a second temperature and a second pressure for a second time period.

Advantageously, by bonding the comfort layer in a second, separate, step, the conditions of temperature, pressure and time required to create a strong bond between the walls of the cavity and between the comfort layer and the cavity wall can be less harsh (lower temperature, lower pressure and/or shorter time period) for both welds as compared to joining the cavity walls and the comfort layer in a single welding step. This can reduce the risk of damage to the cavity walls, or more beneficially, to the comfort layer for which the feel and appearance are considered important characteristics.

According to a another aspect of the present invention there is provided a method of forming an ostomy pouch; the method comprising: providing a film to form a first cavity wall and a second cavity wall; providing a comfort material to form a comfort layer; wherein the comfort material is a fabric material with a hot melt adhesive coating thereon; joining a first cavity wall to a second cavity wall at a first temperature and a first pressure for a first time period; and subsequently, joining a comfort layer to at least one of the first and second cavity walls at a second temperature and a second pressure for a second time period.

Advantageously, the provision of a hot melt adhesive backed comfort layer removes the need to substitute the normal materials for different, specialist materials, and the need for additional intervening layers which reduces the production complexity and cost of the pouch and makes it more discreet and comfortable for the user to wear. In addition, the hot-melt adhesive also supports the comfort layer (which may be woven) and prevents undesirable breakdown of the layer such as fraying, and it moves with the comfort layer and hence does not rustle. Furthermore, the hot melt adhesive can provide increased stability to the comfort material during processing of the material down an automated manufacturing line. Still further, testing has been performed in the lab which suggests that the use of a hot melt adhesive (such as EVA in the tests) on one or more panels of the comfort material aids in the reduction of 'sagging' of the pouch when full.

As noted above, advantageously, the use of a two-step welding process allows the joining of the plastics films of the first cavity wall and the second cavity wall and the joining of the comfort layer to the cavity walls to be performed under less harsh conditions as compared to welding all of the layers simultaneously. This allows the layers to be joined with a reduced risk of damage. In particular, the gentler conditions can avoid or reduce leakage of the hot-melt adhesive through the fabric of the comfort material, which may be visually unappealing, or unappealing to the touch.

The comfort material may be a woven fabric material.

According to first aspect of the present invention there is provided a method of forming an ostomy pouch; the method comprising: providing a film to form a first cavity wall and a second cavity wall; providing a comfort material to form a comfort layer; wherein the comfort material is a woven fabric material with a hot melt adhesive coating thereon;

joining a first cavity wall to a second cavity wall at a first temperature and a first pressure for a first time period; and subsequently, joining a comfort layer to at least one of the first and second cavity walls at a second temperature and a second pressure for a second time period.

Including a hot-melt adhesive backing/coating is especially beneficial where the comfort material is woven, as these are particularly susceptible to fraying etc. whilst the (at least) two-step manufacturing process, is of particular benefit in this scenario, as a woven material can be more susceptible to seepage of molten adhesive through from the hidden side (attached to the cavity) to the, visible, outside surface (and the gentler conditions avoid/reduce this).

Optional features as set out below may apply to any aspect of the invention as appropriate.

The first temperature may be greater than the second temperature; and/or the first pressure may be greater than the second pressure; and/or the first time period may be greater than the second time period.

It will be understood that this can be broken down into three options, which may of course be combined; i.e. (i) the first temperature may be greater than the second temperature; (ii) the first pressure may be greater than the second pressure; (iii) the first time period may be greater than the second time period.

The first temperature may be greater than the second temperature and the first pressure may be greater than the second pressure (i.e. the conditions of temperature and pressure are both harsher in the first step). Alternatively, the first temperature may be greater than the second temperature and the first pressure may be less than the second pressure. Alternatively, the first temperature may be greater than the second temperature and the first pressure may be equal to the second pressure. The first temperature may be greater than the second temperature and the first time period may be greater than the second time period (i.e. the conditions of temperature and duration are both harsher in the first step). Alternatively, the first temperature may be greater than the second temperature and the first time period may be less than the second time period. Alternatively, the first temperature may be greater than the second temperature and the first time period may be equal to the second time period. It is advantageous that the first time period and the second time period be equal as this allows the two steps on the assembly line to be in sync and neither cause a bottleneck for the other.

The first temperature may be greater than the second temperature, the first pressure may be greater than the second pressure and the first time period may be equal to the second time period (i.e. the conditions of temperature and pressure are both harsher in the first step). It is advantageous that the first time period and the second time period be equal as this allows the two steps on the assembly line to be in sync and neither cause a bottleneck for the other. Alternatively, the first temperature may be greater than the second temperature, the first pressure may be greater than the second pressure and the first time period may be greater than the second time period. Alternatively, the first temperature may be greater than the second temperature, the first pressure may be greater than the second pressure and the first time period may be less than the second time period. Alternatively, the first temperature may be greater than the second temperature, the first pressure may be less than the second pressure and the first time period may be less than the second time period. Alternatively, the first temperature may be greater than the second temperature, the first pressure may be less than the second pressure and the first time period may be greater than the second time period. Alternatively, the first temperature may be greater than the second temperature, the first pressure may be less than the second pressure and the first time period may be equal to the second time period. Alternatively, the first temperature may be greater than the second temperature, the first pressure may be equal to the second pressure and the first time period may be less than the second time period. Alternatively, the first temperature may be greater than the second temperature, the first pressure may be equal to the second pressure and the first time period may be greater than the second time period. The first temperature may be greater than the second temperature, the first pressure may be equal to the second pressure and the first time period may be equal to the second time period. Only the temperature varying between the two joining steps can be advantageous as it reduces the number of variables thereby simplifying the process.

The first pressure may be greater than the second pressure and the first time period may be equal to the second time period. Again, it is advantageous that the first time period and the second time period be equal as this allows the two steps on the assembly line to be in sync and neither cause a bottleneck for the other, and the second pressure being less harsh than the first reduces the possibility of the hot melt adhesive seeping through the comfort material. Alternatively, the first pressure may be greater than the second pressure and the first time period may be greater than the second time period. Alternatively, the first pressure may be greater than the second pressure and the first time period may be less than the second time period. Alternatively, the first pressure may be greater than the second pressure and the first temperature may be less than the second temperature. Alternatively, the first pressure may be greater than the second pressure and the first temperature may be equal to the second temperature.

In one embodiment the first pressure is greater than the second pressure, the first temperature is less than the second temperature and the first time period is greater than the second time period. Alternatively, the first pressure is greater than the second pressure, the first temperature is less than the second temperature and the first time period is less than the second time period. Alternatively, the first pressure is greater than the second pressure, the first temperature is less than the second temperature and the first time period is equal to the second time period.

In another embodiment the first pressure is greater than the second pressure, the first temperature is equal to the second temperature and the first time period is greater than the second time period. Alternatively, the first pressure is greater than the second pressure, the first temperature is equal to the second temperature and the first time period is less than the second time period. Alternatively, the first pressure is greater than the second pressure, the first temperature is equal to the second temperature and the first time period is equal to the second time period.

In other embodiments, the first time period is greater than the second time period and the first temperature is less than the second temperature. Alternatively, the first time period is greater than the second time period and the first temperature is equal to the second temperature. Alternatively, the first time period is greater than the second time period and the first pressure is less than the second pressure. Alternatively, the first time period is greater than the second time period and the first pressure is equal to the second pressure.

In a further embodiment, the first time period is greater than the second time period, the first pressure is less than the second pressure and the first temperature is less than the second temperature. Alternatively, the first time period is greater than the second time period, the first pressure is less than the second pressure and the first temperature is equal the second temperature. Alternatively, the first time period is greater than the second time period, the first pressure is equal to the second pressure and the first temperature is less than the second temperature. Alternatively, the first time period is greater than the second time period, the first pressure is equal to the second pressure and the first temperature is equal to the second temperature.

In a preferred embodiment, the first temperature is less than the second temperature, the first pressure is equal to the second pressure and the first time period is equal to the second time period.

Advantageously, the first, harsher, conditions can create a strong bond between the walls of the cavity (typically formed of a plastics film), whilst the second, gentler conditions can attach a comfort layer without damaging the comfort layer, or creating visual imperfections in the comfort layer. Of course, the strong bond between the walls of the cavity is important to the integrity of the pouch, whilst the strength of the bond between the comfort layer and the walls is less important than its feel and appearance. In particular, the gentler conditions can avoid or reduce leakage of the hot-melt adhesive through the fabric of the comfort material, which may be visually unappealing, or unappealing to the touch.

The first temperature may be between 100° C. and 150° C., preferably between 110° C. and 130° C. and more preferably 120° C. The second temperature may be between 130° C. and 160° C., preferably between 140° C. and 150° C. and more preferably 145° C. Alternatively, the second temperature may be between 90 and 140° C., such as 100-120° C., e.g. 110° C.

The first pressure may be between 2.5 bar and 3 bar preferably between 2.6 bar and 2.8 bar, for example 2.7 bar. The second pressure may be between 2.5 bar and 3 bar preferably between 2.6 bar and 2.8 bar, for example 2.7 bar.

The first time period may be between 500 ms and 750 ms preferably 500 ms. The second time period may be between 500 ms and 750 ms preferably 500 ms.

The join between the first cavity wall and second cavity wall may overlap the join between the comfort material and at least one of the first and second cavity walls. This creates a neat appearance, which is important given the aim of discretion and the intention that the appliance, if noticed, might be though to be an undergarment.

The join between the first cavity wall and second cavity wall may be offset from the join between the comfort material and at least one of the first and second cavity walls. This improves the strength of the joins as the second join is formed with material which has not been affected by a previous weld.

The method may further comprise providing a first comfort layer and a second comfort layer. The first comfort layer may be joined to the first cavity wall. The second comfort layer may be joined to the second cavity wall. The first comfort layer may be a rear comfort layer. The first cavity wall may be a rear cavity wall. The first cavity wall may comprise an inlet for receiving stomal output. The first comfort layer may comprise an opening corresponding to the inlet. The second comfort layer may be a front comfort layer. The second cavity wall may be a front cavity wall.

One of the comfort layers may be joined concurrently with the joining of the first and second cavity walls. The comfort layer joined concurrently with the joining of the first and second cavity walls may be a body facing, rear, comfort layer. For example, the first cavity wall may be a body-facing, rear, cavity wall, comprising an inlet for receiving stomal output into the cavity; and the first comfort layer may be a body-facing, rear, comfort layer, which is joined to the first cavity wall concurrently with the joining of the first and second cavity walls. The second cavity wall may be a front cavity wall, facing away from the body; and the second comfort layer may be a front comfort layer, which may be joined subsequently to the joining of the cavity walls. This is advantageous because it simplifies the manufacturing process by reducing the number of joining steps required to two. Although the risk of seepage of hot melt adhesive will be increased for the body facing comfort layer, this is of less concern as it faces the user and the front comfort layer is more likely to be seen.

Alternatively, the first and second comfort layers may be joined to the cavity walls concurrently. This can be an efficient process, requiring only two steps (a first one to join the cavity walls, and a subsequent one to join both comfort layers to the cavity walls). This allows for the joining of the cavity walls to be done using harsher conditions of temperature, pressure and time to ensure a sufficient weld, without risking the seepage of hot melt adhesive through the comfort material, which can later be joined under less harsh conditions (or at least conditions that are less harsh than would be necessary for the heat and pressure to pass through the comfort layers to join the cavity walls too in a single action).

As a further alternative, the first and second comfort layers may be joined sequentially after joining the cavity walls. That is to say, the cavity walls may be joined, then one comfort layer may be joined before the other (in a three-step process). This is beneficial where it is desirable to use different conditions to join the two comfort layers, for example where two different comfort materials and/or hot melt adhesives are used for the front and rear comfort layers. This approach may also simplify the apparatus required, not requiring machines to be capable of forming two bonds simultaneously.

The method may further comprise arranging a or the comfort layer with the hot melt adhesive adjacent to a or the cavity wall prior to joining. A portion of the comfort layer may remain unbonded to the cavity wall. For example, the sheet of comfort material may be bonded to the outside surface of the cavity wall at the periphery, but unbonded to the wall other than at the periphery. The hot melt adhesive may face the exterior of the cavity. At least part of the hot-melt adhesive on the inside surface of the comfort material may be adjacent, facing and unbonded to the outside surface of a wall (e.g. the front wall) forming the exterior of the cavity.

The method may comprise coating the at least part of one side of the comfort material with hot-melt adhesive to form a coating, or "backing". The method may comprise applying the hot melt adhesive as a web. The hot-melt adhesive coating may be applied by any suitable method. The hot-melt adhesive may be applied by: roll coating; scatter coating; extrusion coating; spray coating; slot coating; or foam-in-place coating.

The method may comprise applying the hot melt adhesive coating to the comfort material prior to joining the comfort material to at least one of the cavity walls. The step of applying the hot melt adhesive to one side of a sheet of woven comfort material may be conducted separately from the step of bonding the inside surface of the sheet of woven comfort material to a wall of the pouch. For example, it may be conducted temporally separately, e.g. a least 5 minutes, 10 minutes, 1 hour, 12 hours, of 24 hours before bonding the inside surface of the sheet of comfort material to the wall. This allows the hot-melt adhesive to be dry when the sheet of woven comfort material is handled, thus enhances handleability (whereas involving a wet adhesive in the process would make handling more difficult). Alternatively/additionally, the step of applying hot melt adhesive to one side of a sheet of woven comfort material may be conducted physically separately from the step of bonding the inside surface of the sheet of woven comfort material to a wall of the pouch. For example it may be conducted in a separate room, separate building or separate city, county or state. Similarly this separation of wet adhesive from the place where the pouches are formed has benefits in terms of cleanliness and simplicity.

The, or a, comfort layer may comprise two or more parts. Where the comfort layer comprises two or more parts, the method may include arranging a plurality of sheets of comfort material, each associated with one part. The method may include joining the sheets of comfort material to the pouch. The joining may be performed simultaneously.

The first and second cavity walls may be joined by heat welding. The one or more comfort layers may be joined by heat activated adhesion. The hot melt adhesive may partially penetrate the comfort material. By penetrating the comfort material the hot melt adhesive provides a stronger bond.

The temperature and/or pressure may be applied by at least one die. The temperature and/or pressure may be applied by two dies on opposing sides of the join. By applying the temperature and/or pressure from both sides of the join a superior join may be achieved, it may also reduce the temperature that need be applied by the first die as the heat from the first die need not penetrate through the entire join. A first die may have a higher temperature than a second die. Where one comfort layer is provided, the first die may be applied to the cavity wall and the second die to the comfort layer. Where two comfort layers are provided, the first die may be applied to a body facing comfort layer and the second die to an outward facing comfort layer. By applying the cooler die to the visible side of the pouch in use a strong join can be assured by the higher temperature die but the risk of visible seepage reduced by using a cooler die on the visible side.

Preferably, the first cavity wall and the second cavity wall are formed from separate sheets of plastics film. Alternatively, the first cavity wall and the second cavity wall a formed from a single sheet of plastics film, for example by folding the sheet of plastics films in two prior to welding.

The woven comfort material may comprise a natural material, for example cotton or wool and/or a synthetic material, for example any one or more of polyester, nylon, viscose, polyethylene, polypropylene, or the like. The woven material may have an area density of 20 to 200 g/m$^2$, preferably 40-80 g/m$^2$, for example 58 g/m$^2$. The woven material may have a tensile strength of 200 to 400 N, preferably 250 to 350 N, for example 300N in the warp and 280N in the weft. The woven material may have a tear strength of 5 to 50 N, preferably 10-30N, for example 18 N. The woven material may have a colour fastness to any one or more of rubbing, perspiration or washing (40°) of 4 to 5. The woven material may have an abrasion of >50,000. The woven material may have a water resistant finish. For example, it may comprise woven polyester with a water repellent finish. The water repellent finish may be fluorocarbon based. The water repellent finish may be dyed heat set or boil off heat set.

The hot-melt adhesive may comprise any suitable type of hot-melt adhesive.

The hot-melt adhesive may comprise one or more of a polyolefin, ethylene-vinyl acetate (EVA), polyurethane, polyvinylidene chloride (PVDC), silicon rubber, fluoropolymers, polycarbonate, styrene block co-polymer, polyester, polyamide, or polycaprolactone. In particular it may comprise EVA or co-polyester. In one embodiment the hot-melt adhesive is a polyolefin. In one embodiment the hot-melt adhesive is ethylene-vinyl acetate (EVA). In one embodiment the hot-melt adhesive is polyurethane. In one embodiment the hot-melt adhesive is polyvinylidene chloride (PVDC). In one embodiment the hot-melt adhesive is silicon rubber. In one embodiment the hot-melt adhesive is a fluoropolymer. In one embodiment the hot-melt adhesive is polycarbonate. In one embodiment the hot-melt adhesive is styrene block co-polymer. In one embodiment the hot-melt adhesive is polyester. In one embodiment the hot-melt adhesive is polyamide. In one embodiment the hot-melt adhesive is polycaprolactone. The hot melt-adhesive may have an area density of at least 5, 10, 15, 16 or 20 g/m$^2$, and/or no more than 50, 40, 35, 30 or 25 g/m$^2$ preferably 10-50 g/m$^2$, 16-35 g/m$^2$, 20-30 g/m$^2$, or 23-27 g/m$^2$, for example 25 g/m$^2$.

The woven comfort layer may have a thickness of 50 to 1000 micrometres, preferably 60 to 500 micrometres, more preferably 75 to 300 micrometres.

The hot-melt adhesive may have a maximum thickness, or an average (mean) thickness of less than 0.05 mm, less than 0.04 mm, less than 0.03 mm, less than 0.02 mm, 20 or less than 0.0.01 mm, for example less than 0.005 mm.

The web of hot melt adhesive may comprise a mass and a plurality of voids in the mass. The web may be a lattice, mesh, or grid. The web may be a net or dots. The voids may be regularly spaced. The voids may be irregularly spaced. The voids may be regularly shaped. The web may have a regular and consistent distribution of adhesive. The voids may be irregularly shaped. The web may have an irregular and inconsistent distribution of adhesive. Each void may contain an absence (i.e. a substantial absence) of hot-melt adhesive applied to the woven fabric layer compared to the mass. The voids may make up at least 20%, at least 30%, at least 40%, at least 50%, at least 60%, or at least 70% of the web.

A web of this type can thus be much thinner and/or made of much less material than a full film, as well as avoiding the rustling associated with films.

Therefore, by selecting these appropriate web properties, the mechanical properties of the comfort layer can be tuned. This increases the comfort for the user as the comfort layer's mechanical properties and the properties of the pouch as a whole, can be optimised so that it conforms to the body better than a pouch with more layers, provides a pleasant feel on the skin, and so forth.

The inside surface of the sheet of woven comfort material may be divided into one or more regions. The hot-melt adhesive may be applied to the region or one or more regions. Where there are two or more regions, specific properties of the web may be selected for each region. One or more of the regions may not have hot-melt adhesive applied to them. Therefore, the web can be selectively applied to areas of the pouch and the properties of the web can be adapted to suit the area of the pouch it is applied to. This allows the mechanical and adhesive properties of the web to be optimised depending on its location on the pouch which further enhances the performance of the pouch.

A web of hot-melt adhesive may coat at least the upper part of the rear surface facing towards the ostomate in use; and a web of hot melt adhesive may coat at least the upper part of the layer of woven comfort material covering the front of the pouch this has been found to be particularly effective in reducing sagging.

A web of hot-melt adhesive may coat at least the upper 10%, 20%, 30%, 40% or 50% of the rear surface facing towards the ostomate in use. A web of hot melt adhesive may coat at least the upper 10%, 20%, 30%, 40% or 50% of the layer of woven comfort material covering the front of the pouch.

At least a lower part of the layer of comfort material covering the front of the pouch may be not provided with a web of hot-melt adhesive. At least the lower 10%, 20%, 30%, 40% or 50% may be uncoated with a web of hot-melt adhesive. This can reduce cost as the lower part does not require the application of hot-melt adhesive and can achieve the same result in terms of avoiding sagging, possibly even better results, on account of a stiffer (coated) part at the top serving to reduce the likelihood of that part sagging, whilst a less stiff (uncoated) front lower part is more easily deformed.

Alternatively, the hot melt adhesive may be applied to the entirety (i.e. substantially the entirety) of the inside surface of the comfort material—this of course is easier to mass-produce than having to select particular areas to coat, and given the thinness of the web of adhesive and the presence of voids, it still involves applying a relatively small amount of material, certainly as compared to a complete film layer as in the prior art. The pouch may comprise at least one sheet of comfort material with the hot melt adhesive applied thereto (for example to its entirety) and at least one sheet of comfort material without the hot melt adhesive applied thereto. It may comprise at least two sheets of comfort material with the hot melt adhesive applied thereto and at least one sheet of comfort material without the hot melt adhesive applied thereto.

One or more regions where the hot melt adhesive is coated may include at least part of a periphery of the sheet of woven comfort material. The periphery of the sheet of woven comfort material may be aligned with the periphery of the pouch. Therefore, the pouch and comfort material can be welded together in a single weld that seals the pouch around its perimeter, maximising the capacity of the pouch.

Where the comfort material comprises polyester and the hot melt adhesive comprises ethylene-vinyl acetate (EVA) the first temperature may be between 100° C. and 150° C., preferably between 110° C. and 130° C. and more preferably 120° C. Where the comfort material comprises polyester and the hot melt adhesive comprises ethylene-vinyl acetate (EVA) the second temperature may be between 130° C. and 160° C., preferably between 140° C. and 150° C. and more preferably 145° C. Alternatively the second temperature may be between 90 and 140° C., such as 100-120° C., e.g. 110° C.

Where the comfort material comprises polyester and the hot melt adhesive comprises ethylene-vinyl acetate (EVA) the first pressure may be between 2.5 bar and 3 bar, preferably between 2.6 bar and 2.8 bar, for example 2.7 bar. Where the comfort material comprises polyester and the hot melt adhesive comprises ethylene-vinyl acetate (EVA) the second pressure may be between 2.5 bar and 3 bar, preferably between 2.6 bar and 2.8 bar, for example 2.7 bar. Where the comfort material comprises polyester and the hot melt adhesive comprises ethylene-vinyl acetate (EVA) the first time period may be between 500 ms and 750 ms, preferably 500 ms. Where the comfort material comprises polyester and the hot melt adhesive comprises ethylene-vinyl acetate (EVA) the second time period may be between 500 ms and 750 ms, preferably 500 ms.

A further component may be attached to the inside or outside surface of the woven comfort material. The region, or one or more of the regions where the hot melt adhesive is coated may be arranged to attach the further component to the woven comfort material. The further component may be arranged on the outside opposite the or a region of the hot melt adhesive or the inside. The further component may be attached to the woven comfort material by a weld. The weld may be facilitated by the hot-melt adhesive on the inside surface of the woven comfort material seeping through to bond to the component on the outside. At least some of the hot-melt adhesive may fully penetrate the fabric layer of the woven comfort material on welding. The hot-melt adhesive may adhere to the further component and fabric layer on welding. Therefore, the present invention provides convenient means for securing additional components to the pouch that can increase the functionality of the pouch. The join to a further component may be conducted under harsher conditions of temperature, pressure and/or time than the join between the comfort layer and the cavity wall. This way at least some of the adhesive fully penetrates the comfort layer to assist in attaching the component, but in the region of the join between the comfort layer and the cavity wall (which may be visible), the adhesive does not fully penetrate the comfort layer, and is not visible (although it may partially penetrate the comfort layer, to improve the bond).

The rear cavity wall and front cavity wall may be substantially the same shape. The rear cavity wall and front cavity wall may be joint at their peripheries. The rear wall and front wall may be formed of flexible sheet material, for example plastics film. The rear wall and/or front wall may be opaque. The rear wall and/or front wall may be transparent. In particular at least part of the front wall may be transparent. The film may be formed for example of any one of polyurethane, polyethylene (PE), polyvinylidene chloride (PVDC), or ethylene-vinyl acetate (EVA). The film may have a thickness of 50 to 150 μm. The film may have a thickness of 75 to 100 μm. The rear wall and front wall may have corresponding inside and outside surfaces. The inside surfaces of the rear and front walls may form the interior of the cavity. The outside surfaces of the rear and front walls may form the exterior of the cavity. The sheet of woven comfort material may cover the outside surface of the front wall. The sheet of woven comfort material may be substantially the same shape as the front wall.

A/the layer of woven comfort material covering the front of the pouch may comprise one or more parts. A/the layer of woven comfort material covering the front of the pouch may comprise an upper part and a lower part. The upper part and lower part when taken together may be the same shape as the front wall. The upper part may extend from a top edge of the pouch to a point 20-50% down its length from the top. The lower part may extend from a bottom edge of the pouch to a point 15-50% down its length from the top. An overlap region may be provided where the upper part and lower part overlap. The upper part may extend over the lower part (or vice versa) to form the overlap in the overlap region. The hot melt adhesive may be provided on one or both parts in the overlap region. In particular, the hot-melt adhesive may be provided on one or both parts at a periphery of the pouch, so as to ensure that these edges of the overlap region are bonded and the overlying part does not flap around. The upper part and the lower part may be separable from each other in the overlap region. The overlap region may extend horizontally when the ostomy pouch is in use. Thus, especially when the front wall is formed of a transparent film, the present invention provides a device that can permit convenient viewing of the stoma and/or the contents of the pouch if required.

In addition, the free edges of upper and lower parts of the woven comfort material are protected from fraying by the hot-melt adhesive applied to the inside surface. This is effective where the entire inside surface has hot-melt adhesive applied thereto. However, embodiments may have hot melt adhesive applied in regions, in which the regions comprise the free edges of the top and bottom parts of the layer of woven material covering the front of the pouch.

The pouch may comprise a drain. The drain may be disposed at the bottom of the pouch in use. The drain may be formed from the front and rear walls of the pouch. The drain may be rectangular. The drain may be foldable. The drain may be foldable along its length. The drain may be movable between a folded and unfolded configuration. The drain may be in a closed state in its folded configuration. The drain may be in an open state in its unfolded configuration. When open, the drain may permit stomal output to leave the cavity of the pouch. When closed, the drain may prevent stomal output leaving the cavity of the pouch.

The drain may be provided with one or more pursing strips. The or each pursing strip may span the width of the drain. The or each pursing strip may extend the same distance along the length of the drain. The or each pursing strip may provide localised rigidity to the drain. The or each pursing strip may be formed from polystyrene. The or each pursing strip may define the locations and orientations of one or more folds of the drain. The or each pursing strip may comprise a strip of flexible material attached drain. The strip may have a higher rigidity than the material of the drain. The or each pursing strip may have some resilience once attached to the drain. Therefore, the pursing strips can be squeezed laterally to arch the pursing strip and thereby assist in opening the drain.

A pursing strip may be provided on the rear wall. The pursing strip may be provided adjacent a bottom end of the drain. The pursing strip may be provided on the outside surface of the rear wall. A pursing strip may be provided on the front wall. The front wall pursing strip may be provided on the outside surface of the front wall. The front wall pursing strip may be provided above the rear wall pursing strip. The front wall pursing strip may be provided midway between a top end and the bottom end of the drain. A longitudinal gap may be provided between an upper edge of the rear wall pursing strip and a lower edge of the front wall pursing strip. The longitudinal gap may define the location of a first fold of the drain.

A fastening element may be disposed on an outside surface of the rear wall. The rear fastening element may be disposed above the front pursing strip. A longitudinal gap may be provided between an upper edge of the front wall pursing strip and a lower edge of the second fastening element. The longitudinal gap may define the location of a fold of the drain. The rear fastening element may be disposed adjacent the top end of the drain.

A further component attached to a sheet of comfort material as set out above may be a closure mechanism for the drain of the ostomy pouch. The closure mechanism may be attached to a sheet of comfort material covering the front of the pouch. The closure mechanism may be attached to the outside surface of the comfort material. The closure mechanism may be a closure flap. The closure flap may be welded to the woven comfort material. It may be welded opposite a region of hot melt adhesive. The weld may be along a top edge of the closure flap. The closure flap may have an outside surface and an inside surface. The inside surface of the closure flap may be adjacent the outside surface of the comfort material. The closure flap may comprise a front fastening element. The front fastening element may co-operate to fasten with the rear fastening element. Fastening of the fastening elements may close the drain.

The closure flap (or further component generally) may comprise a plastic foam material. This is desirable as it imparts a rigidity desirable in a closure flap in particular, to keep the folded drain flat.

The closure flap (or further component generally) may comprise a woven comfort material (optionally comprising the hot-melt adhesive, e.g. a web thereof having the features set out above). This is desirable as forming the closure flap of the same material as the comfort material makes it more subtle/discreet.

The closure flap may extend across the majority of the width of the pouch. It may conform to the shape of the pouch. It may be arranged adjacent a peripheral weld between the front comfort layer and the front wall. Extending across substantially all of the width of the pouch is unusual because normally closure flaps are attached not to the comfort material but to the material of the drain and must therefore be much narrower than the width of the pouch.

The front fastening element may be disposed above the rear fastening element. The front fastening element may be disposed adjacent a bottom edge of the comfort material. A longitudinal gap may be provided between an upper edge of the rear fastening element and a lower edge of the front fastening element. The longitudinal gap may define the location of a fold of the drain. The rear fastening element may be disposed adjacent the top end of the drain.

The drain may be closed by repeatedly folding the drain upwards about the fold lines defined by the front and rear pursing strips and front and rear fastening elements. The folded drain may be retained between the woven comfort material and closure flap. The sides of the closure flap may not extend beyond the edges of the comfort material. The closure flap may comprise a tab. The tab may extend beyond the bottom edge of the comfort material. The front and rear fastening elements may be the same size. The front and rear fastening elements may not span the width of the drain.

Therefore, the drain can be conveniently closed against the comfort material and secured in place with the closure flap. It is therefore not necessary to fold or secure the drain beneath the comfort material, making the pouch easier to use. The provision of a tab makes unfolding of the drain easier as the closure flap can be lifted allowing access to undo the fastening elements, as does the inclusion of fastening elements that do not span the entire drain width.

The closure flap may have a contoured outline, for example the outline of a segment of a circle, which can give the base of the pouch a rounded appearance. This is considered preferable as a flat bottom is typically associated with "open" pouches (caused by the folding up of a drain at the bottom) whereas a rounded bottom may be seen as more stylish and not associated with the somewhat unpleasant draining process. Thus, although the pouch may be an open pouch the closure flap may make that less obvious.

DETAILED DESCRIPTION OF THE INVENTION

In order that the invention may be more clearly understood one or more embodiments thereof will now be described, by way of example only, with reference to the accompanying drawings, of which:

In order that the invention may be more clearly understood one or more embodiments thereof will now be described, by way of example only, with reference to the accompanying drawings, of which:

FIG. 4a is a front view of an alternative ostomy pouch.

FIG. 4b is a front view of an alternative arrangement to the ostomy pouch of FIG. 4a.

FIG. 5 is a cross-sectional side view of the ostomy pouch of FIG. 4a.

FIG. 6 is an exploded perspective view of the ostomy pouch of FIG. 4a.

Figure 1:
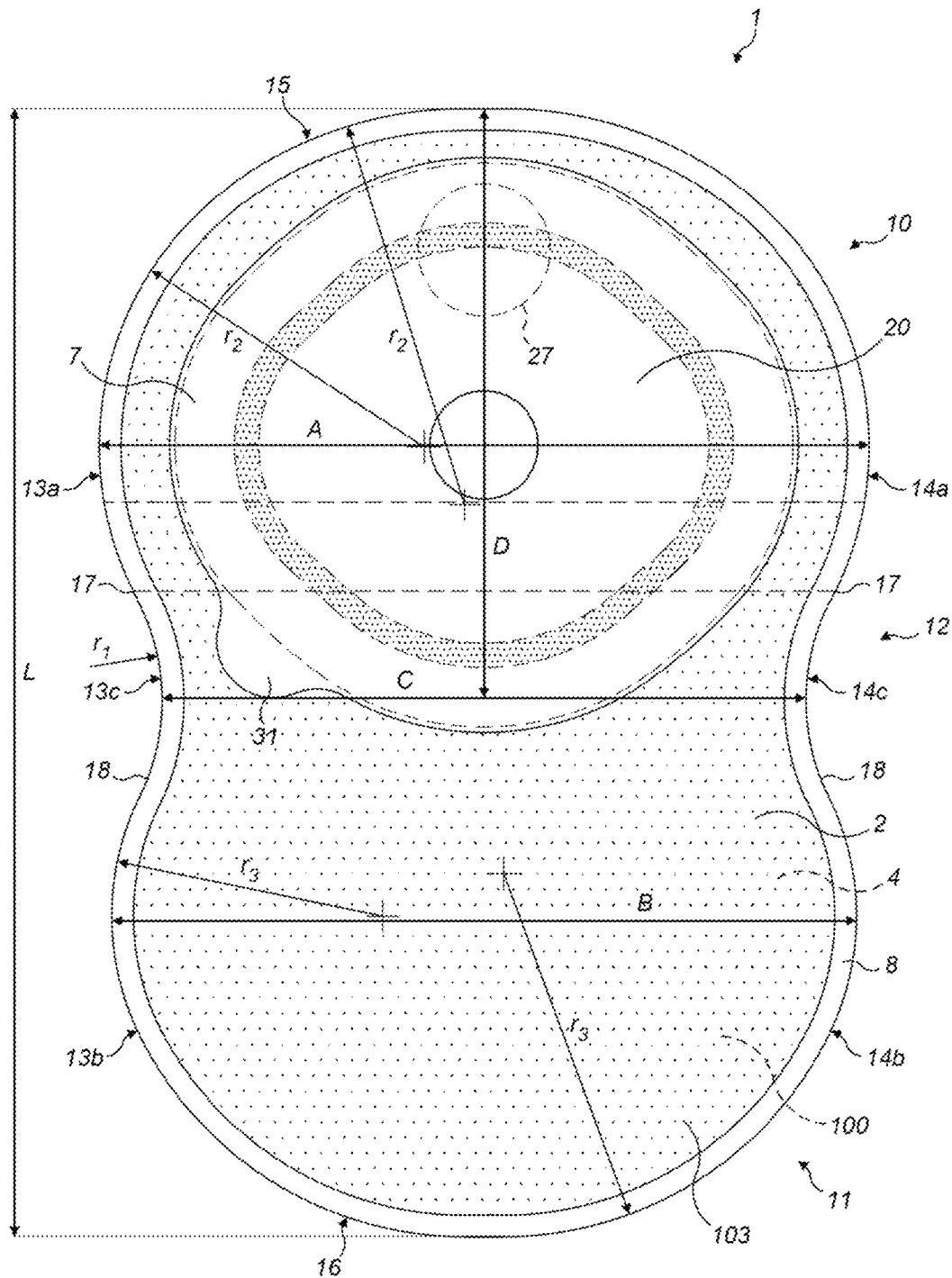
FIG. 1 is a rear view of an ostomy pouch.

The following description is directed to embodiments of the disclosure. The description of the embodiments is not meant to include all the possible embodiments of the disclosure that are claimed in the appended claims. Many modifications, improvements and equivalents which are not explicitly recited in the following embodiments may fall within the scope of the appended claims. Features described as part of one embodiment may be combined with features of one or more other embodiments unless the context clearly requires otherwise.

In this specification, the use of the singular includes the plural unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. For example, "about 5 mm" means "about 5 mm" and also "5 mm." Generally, the term "about" includes an amount that would be expected to be within experimental error. The term "about" includes values that are within 5% less to 5% greater of the value provided. For example, "about 30 mm" means "between 28.5 mm and 31.5 mm."

The main focus of this invention is in the method of forming an ostomy bag, in particular in terms of joining a first cavity wall to a second cavity wall at a first temperature and a first pressure for a first time period; and subsequently, joining a comfort layer to at least one of the first and second cavity walls at a second temperature and a second pressure for a second time period.

However, in order to understand the method, it is useful first to understand the product produced by the method.
Ostomy Pouches Referring to FIGS. 1 to 3, an example of an ostomy pouch produced by the method of the invention is shown in which the ostomy pouch 1 comprises a rear wall 2, a front wall 3, a separation wall 4, a rear comfort layer 5, a front comfort layer 6 and an ostomy wafer 7. In other examples within the ambit of the invention as claimed, one or more of the separation wall 4, the rear comfort layer 5 and the front comfort layer 6 may be omitted if desired.

In this example, the ostomy pouch 1 is a one-piece pouch wherein the ostomy wafer 7 is permanently attached to the ostomy pouch 1 (in the sense that it cannot be easily removed and re-attached without damaging the pouch). However, other examples may be a two-piece pouch comprising a pouch component and body fitment component that together form the ostomy pouch. In some of these examples, the pouch comprises the rear wall 2, the front wall 3, the separation wall 4, the rear comfort layer 5 and the front comfort layer 6, and the body fitment component comprises the ostomy wafer 7.

The rear wall 2 and the front wall 3 define a cavity for containing a stomal output. In this example, the rear wall 2 and the front wall 3 are both formed of flexible sheet material in the form of a plastics film and are joined together to define the cavity. An exemplary film material a coextruded film comprising a Polyvinylidene Chloride (PVdC) layer arranged between two or three layers of Ethylene Vinyl Acetate (EVA) on either side.

In this example, the ostomy pouch 1 has an upper section 10, a lower section 11 and a waisted section 12 that is located between the upper section 10 and the lower section 11. The upper section 10 has a maximum width, A, the lower section 11 has a maximum width, B, and the waisted section, 12, has a minimum width, C. In this example, the maximum width, A, of the upper section 10 is greater than the maximum width, B, of the lower section 11, which in turn is greater than the minimum width, C, of the waisted section 12.

In this example, the ostomy pouch 1 has a left-hand 13 and right-hand 14 edge when viewed from the rear. The waisted section 12 has a left-hand edge 13c and a right-hand edge 14c that are both smoothly rounded and merge into the respective left-hand edges 13a, 13b and right-hand edges 14a, 14b of the upper section 10 and the lower section 11.

The shape and dimensions of the ostomy pouch 1 are not particularly limited so long as it remains discreet and comfortable to wear in use. In this example, the ostomy pouch has a length, L, of 208 mm, maximum width of the upper section A and lower section of 142 mm and 137 mm respectively, and a minimum width of the waisted section C of 119 mm. The minimum width, C, is located at a distance, D, from a top edge of the ostomy pouch 1, in this example D is 119 mm.

In this example, the left-hand edge 13c and the right-hand edge 14c of the waisted section 12 have concave curvature with a radius of curvature, r1, of 40 mm.

In this example, both the upper 10 and lower 11 sections are rounded and comprise continuously curved edges 15, 16 respectively. The curved edges 15, 16 extend from the upper and lower ends of left-hand edge 13c of the waisted section 12 to the corresponding upper and lower ends of the right-hand edge 14c of the waisted section 12. The edges 15, 16 are convexly curved with a radius of curvature of r2 and r3 respectively. In this example, the r2 and r3 are constant along their respective edges 15, 16, however in alternative examples they may be variable. r2 is in the range 55 mm and 75 mm, preferably 60 to 73 mm, and r3 is in the range 45 mm to 70 mm, preferably 50 mm to 67 mm.

In this example, the upper section edge 15 incorporates the left-hand edge 13a and the right-hand edge 14a of the upper section 10 while the lower section edge 16 incorporates the corresponding left-hand 13b and right-hand edge 14b of the lower section.

In this example, a junction between the upper section 10 and the waisted section 12 may be demarcated by a single point of inflection 17 between the edges 13a, 14a of the upper section 10 and the edges 13c, 14c of the waisted section 12. Similarly, a junction between the lower section 11 and the waisted section 12 may be demarcated by a single point of inflection 18 between the edges 13b, 14b of the lower section 11 and the edges 13c, 14c of the waisted section 12.

In this example, the rear wall 2 and the front wall 3 are symmetrical about a vertical midline of the ostomy pouch 1. The rear wall 2 and front wall 3 are joined around their peripheral edges by use of welding.

In this example, the rear wall 2 and the front wall 3 are joined together by a single continuous edge seal 8 that extends around a full perimeter of the rear wall 2 and the front wall 3 to create a fluid-tight seal. The single continuous edge seal 8 has a constant width of 4 mm around the perimeter of the ostomy pouch 1. In other examples, the width may be of different width, for example in the range 3 mm to 5 mm and may also vary around the perimeter.

The rear wall 2 is provided with a stomal inlet 20 for receiving the stomal output into the cavity. The stomal inlet 20 is an aperture that is cut out of the rear wall 2 in the upper section 10 of the ostomy pouch 1, in which the wafer 7 is provided, the wafer having a hole through which a stoma normally extends.

In this example, the rear comfort layer 5 and front comfort layer 6 are substantially the same shape as the rear 2 and front 3 walls. The rear 5 and front 6 comfort layers form the outside of the ostomy pouch 1 and cover the rear 2 and front 3 walls respectively. The rear comfort layer 5 also comprises a wafer aperture that is in register with the stomal inlet 20 of the rear wall 2, in which the wafer 7 is arranged.

Figure 8:
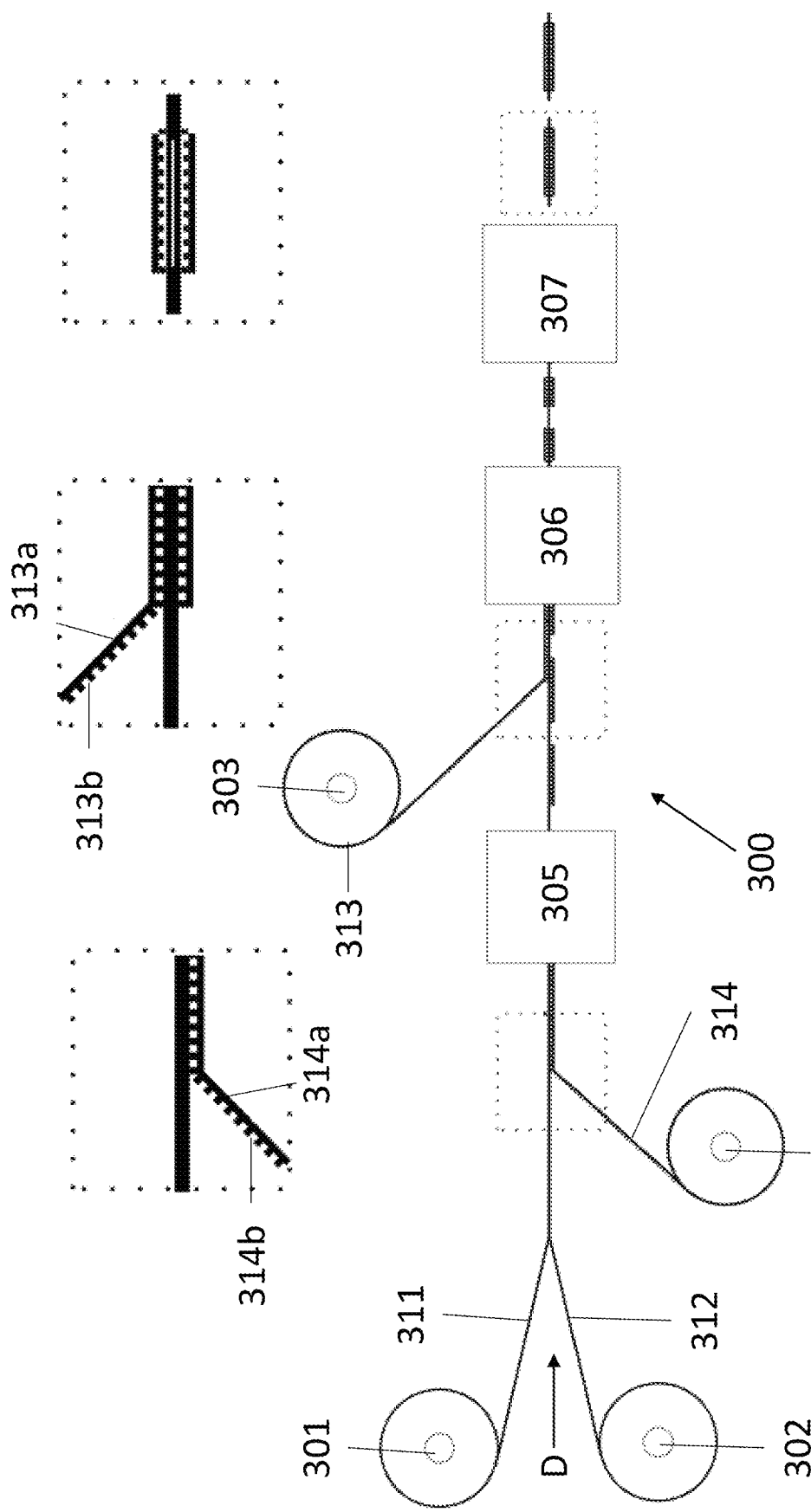
FIG. 8 is a side view of an apparatus for producing an ostomy pouch according to the present invention.

The rear comfort layer 5 and the front comfort layer 6 are formed of a flexible sheet material comprised of a woven fabric layer 50 with a web of hot-melt adhesive 51 coated on one surface—its inside surface in use (see FIG. 8). In this example, the fabric layer 50 forms the outside surface of the rear 5 and front 6 comfort layers respectively, with the web of hot-melt adhesive 51 disposed on the corresponding inside surfaces, facing the rear 2 and front 3 walls. Other examples may comprise additional fabric layers and/or adhesive layers as required. In this example, the woven fabric layer comprises polyester but in other examples any one or more of nylon, viscose, polyethylene and polypropylene could be used in addition or as an alternative.

In this example, the woven fabric layer has an area density of 58 g/m$^2$, a tensile strength of 280 to 300 N, and a tear strength of 18 N. Other examples may have different compositions, for example an area density of 50 to 70 g/m$^2$, a tensile strength of 200 to 400 N, and a tear strength of 10 to 30 N. Some examples may also have a colour fastness to any one or more of rubbing, perspiration or washing (40°) of 4 to 5, and an abrasion of >50,000. Certain examples also comprise a woven polyester with a water repellent finish. The water repellent finish may be fluorocarbon based and may be dyed heat set or boil off heat set. A suitable woven polyester layer is available from Newton Textiles Limited of Northamptonshire, UK, under the 75DCWR Designation, such as 75DCWRWHITE (for a white variant).

In this example, the hot-melt adhesive comprises ethylene-vinyl acetate (EVA).

In another example the hot-melt adhesive is a polyolefin.
In another example the hot-melt adhesive is polyurethane.
In another example the hot-melt adhesive is polyvinylidene chloride (PVDC).
In another example the hot-melt adhesive is silicon rubber.
In another example the hot-melt adhesive is a fluoropolymer.
In another example the hot-melt adhesive is polycarbonate.
In another example the hot-melt adhesive is styrene block co-polymer.
In another example the hot-melt adhesive is polyester.
In another example the hot-melt adhesive is polyamide.
In another example the hot-melt adhesive is polycaprolactone.

In this example, the web of hot-melt adhesive has an area density of 25 g/m$^2$. A suitable EVA hot-melt adhesive is available from Protechnic SA of Cernay, France under the designation 3Z8.

Figure 7:
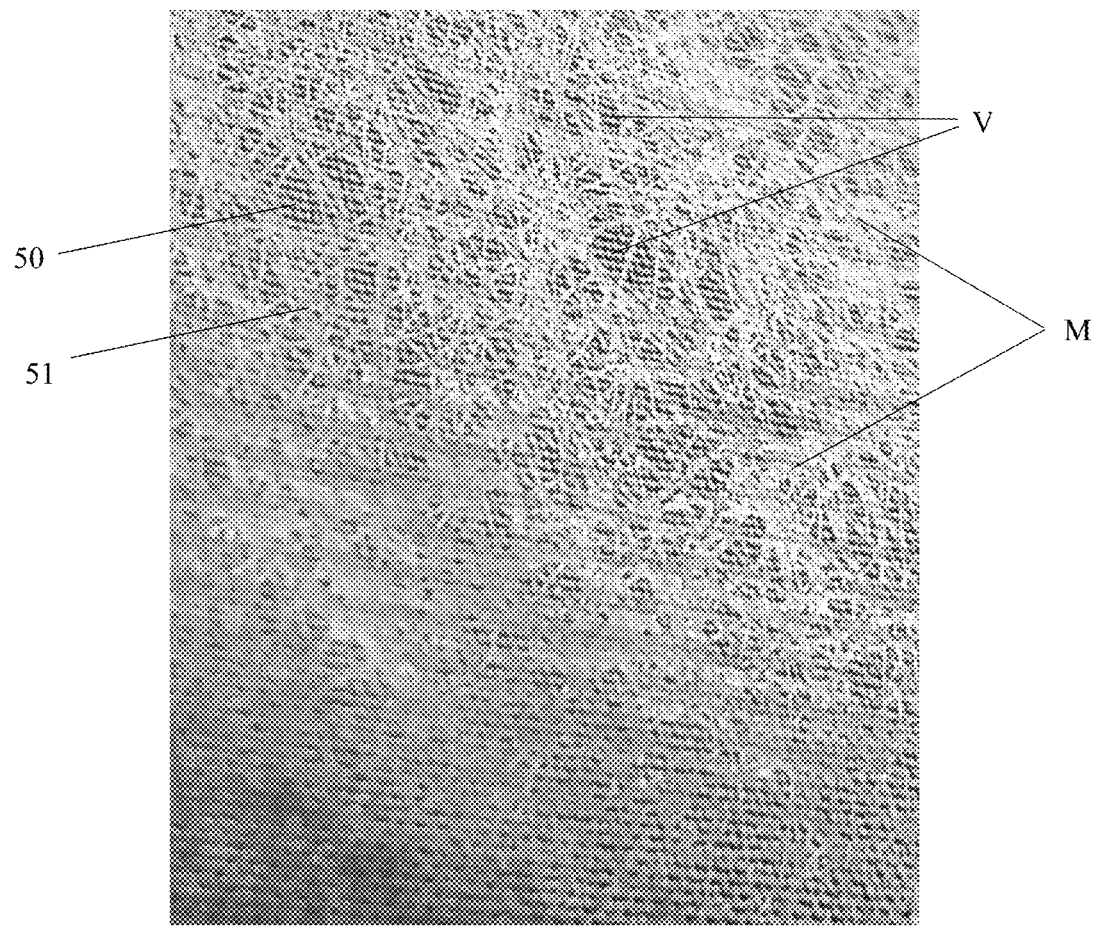
FIG. 7 is a partial view of the inside surface of the woven material which forms the comfort layer of the pouches of FIGS. 1-6 showing the hot-melt adhesive applied thereto.

In this example, the hot-melt adhesive is coated onto the fabric layer over an entire area of the rear 5 and the front 6 comfort layers. In other examples, the hot-melt adhesive may be coated to part of area of the rear 5 and front 6 comfort layers, or specific regions thereof. Where the web is formed, as shown in FIG. 7, it includes a mass M of hot-melt adhesive with numerous voids V therein, where there is an absence (or substantial absence, possibly including a trace) of hot-melt adhesive, thus it takes the general form of a lattice, mesh or grid. As can be seen, in this example the voids are irregularly shaped and spaced and a relatively smaller area is covered by the mass than that which is free of adhesive in the voids. In other examples (not shown) the voids could be regularly shaped and/or regularly spaced.

Advantageously, the use of the hot melt adhesive allows both comfort layers 5,6 to be joined without the need for specialist intervening layers or the application of adhesive during the construction process, improving the join. In this example, the peripheral weld defined by the edge seal 8 comprises a number of individual welds, the first joins the rear comfort layer 5 to the rear wall 2 and the front wall 3, and the second joins the front comfort layer 6 to the other three layers. In other examples, various welds may be used as required or desired. For example, rear comfort layer 5 and front comfort layer 6 could be joined in two separate joins, subsequent to the rear wall 2 and front wall 3 being joined. In addition, the hot-melt adhesive 51 protects the fabric layers 50 from undesirable fraying.

In this example, the front comfort layer 6 comprises an upper part 6a and a lower part 6b, which when taken together are the same shape as the front wall 3. The upper 6a extends from the top of the pouch 1 to the point of inflection 17 between the upper section 10 and waisted section 12. The lower part 6b extends from the bottom of the pouch 1, beneath the upper part 6a to a point slightly above the point of inflection 17. As such, the upper 6a part partially overlaps the lower part 6b in an overlap region 115. The upper part 6a and the lower part 6b are separable from each other in the overlap region 115 to form a window opening for viewing the cavity. The overlap region 115 extends horizontally when the ostomy pouch 1 is in use. In some examples, the overlap region 115 may not coincide with the point of inflection 17 and may span the pouch 1 at any suitable location along its length. Importantly, without the presence of the hot-melt adhesive 51, the two parts 6a, 6b, of the front comfort layer 6 would not bond to one another at all, regardless of the choice of material for the walls 2,3, because the material of the wall is not involved in the bond in that region. This therefore is a key region for the presence of the hot-melt adhesive.

In other example, the front layer 6 may be comprised of multiple parts. The external shape and dimensions of the multiple parts when taken together may be the same as that of the front wall 3.

In this example, the ostomy wafer 7 is in register with the stomal inlet 20 of the rear wall 2 and extends through the wafer aperture of the rear comfort layer 5. The ostomy wafer 7 comprises an adhesive and a release liner 31. The ostomy wafer 7 is mounted to the rear wall 2 by welding. In other examples the wafer 7 may be mounted by any suitable alternative means (e.g. adhesive).

The ostomy pouch 1 may also be provided with a gas vent for venting of stomal gases from the cavity. In this example, the ostomy pouch 1 comprises a gas vent filter 24 which is also an odour filter. Suitable filters could be a charcoal or activated carbon filter, for reducing the release of unwanted odours from the cavity. The gas vent filter 24 forms a part of the gas vent, which comprises a gas vent aperture 27 located in the front wall 3. In some examples, the gas vent filter 24 is covered by a filter cap and the gas vent filter 24 and filter cap are located on the front wall 3 over the gas vent aperture 27. The gas vent aperture 27 permits the passage of gas from the cavity towards an exterior of the ostomy pouch through the gas vent filter 24 and filter cap.

In this example, the gas vent is located, in use, in the upper quarter of the ostomy pouch 1. In particular, the centre of the gas vent aperture 27 is disposed, in use, above the centre of the stomal inlet 20. In other examples, the gas vent may be located elsewhere in the upper section 10 of the ostomy pouch 1.

In this example, the separation wall 4 is located between the rear wall 2 and the front wall 3. The separation wall 4 comprises a separation filter 100 for filtering stomal gases and/or stomal liquids from stomal solids contained in the stomal output. The separation filter 100 thus prevents stomal solids from contacting the gas vent and clogging or otherwise impairing the functionality of the gas vent filter 24.

In this example, the separation wall 4 has the same external shape and dimensions as the rear wall 2 and the front wall 3 and divides the cavity of the ostomy pouch 1 into a first and a second chamber 101, 102. The first chamber 101 extends between the separation wall 4 and the rear wall 2, and the second chamber 102 extends between the separation wall 4 and the front wall 3. The first and second chambers 101, 102 have substantially the same volume. In other examples, they may have different volumes and/or the second chamber 102 may have a larger volume than the first chamber 101.

In this example, the separation wall 4 is joined to the rear wall 2 and front wall 3 at their peripheral edges by use of welding to create a fluid-tight seal therebetween. In another example, the separation wall 4 is joined to the rear 2 and front 3 walls about the whole of the edge of the upper section 10, and is additionally joined to the front wall 3 by a horizontal weld at the interface between the upper 10 and waisted 12 sections. Therefore, the joining of the separation wall 4 with the rear and front walls 2, 3 according to some examples may be such that the first and second chambers 101, 102 are sealed from one another other than via the separation filter 100.

In this example, the separation wall 4 comprises a flexible sheet material, which may be formed of polyurethane, polyethylene (PE), polyvinylidene chloride (PVDC) and/or ethylene-vinyl acetate (EVA). In some examples, the flexible sheet material of the separation wall 4 has a thickness of 50 to 150 micrometres, preferably 75 to 100 micrometres. In this example, the separation wall 4 comprises a hydrophobic and oleophobic coating applied to the flexible sheet material. In other examples, the flexible sheet material may be hydrophobic and/or oleophobic.

Figure 2:
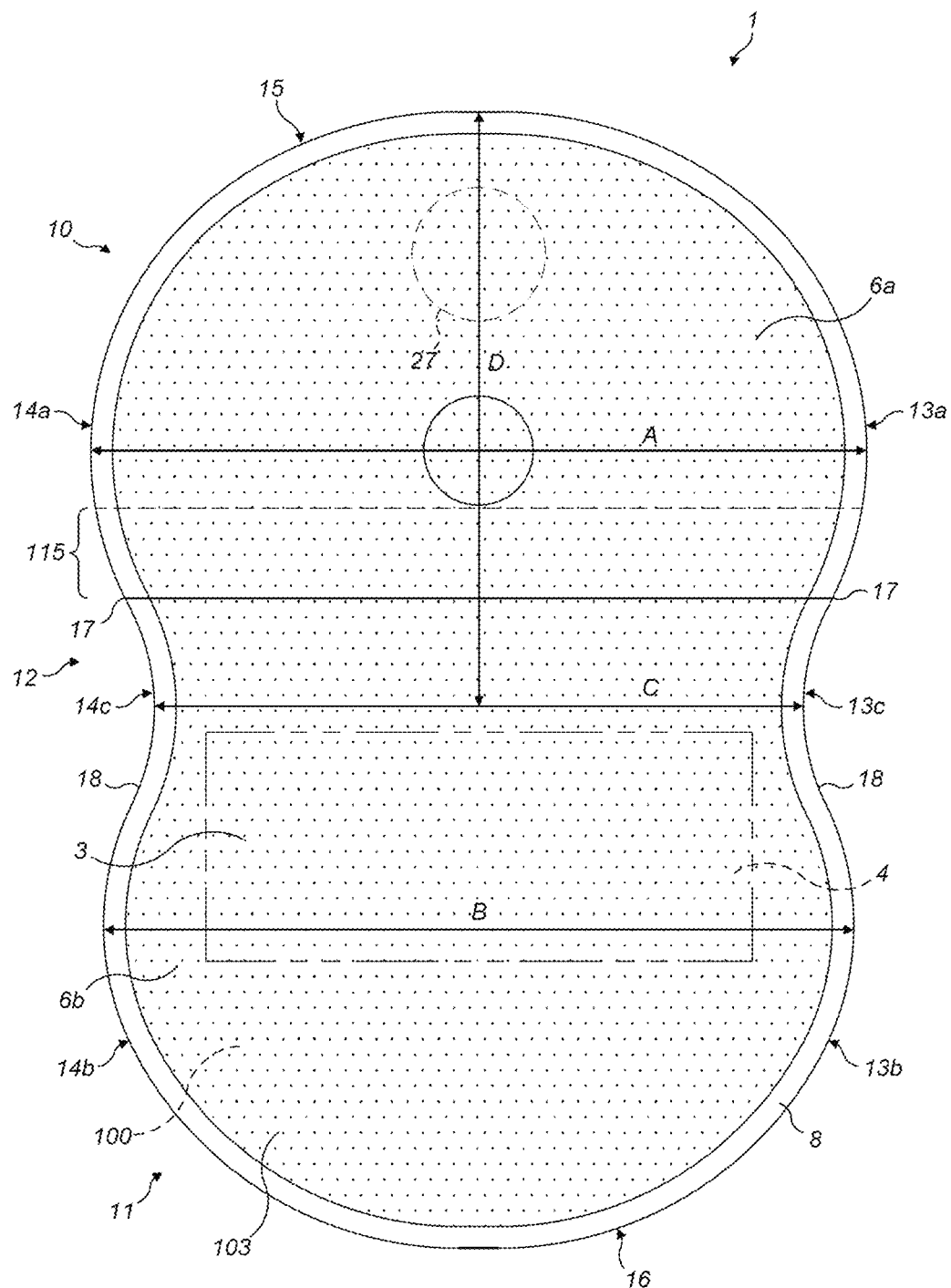
FIG. 2 is a front view of the ostomy pouch of FIG. 1.
Figure 3:
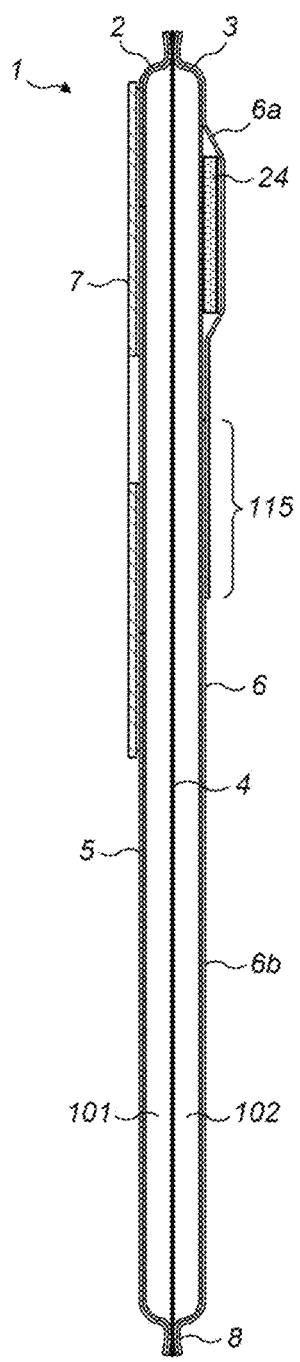
FIG. 3 is a cross-sectional side view of the ostomy pouch of FIG. 1.
Figure 4:
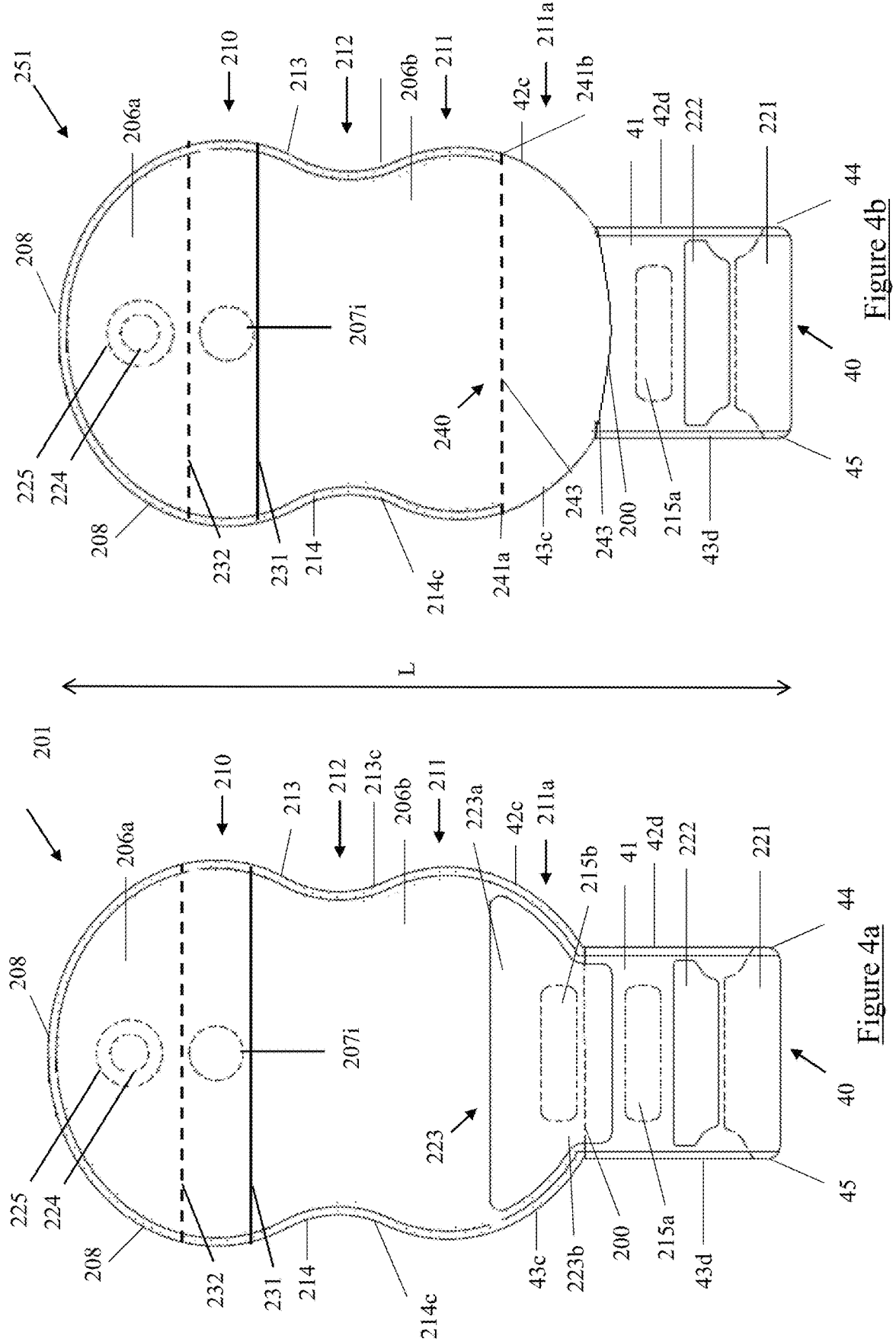
Figure 5:
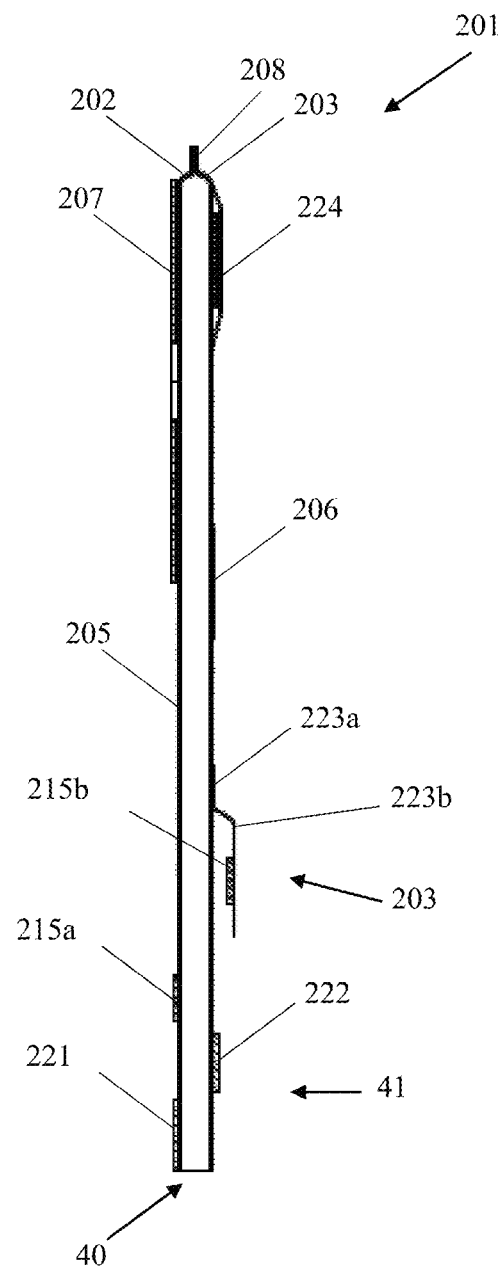
Figure 6:
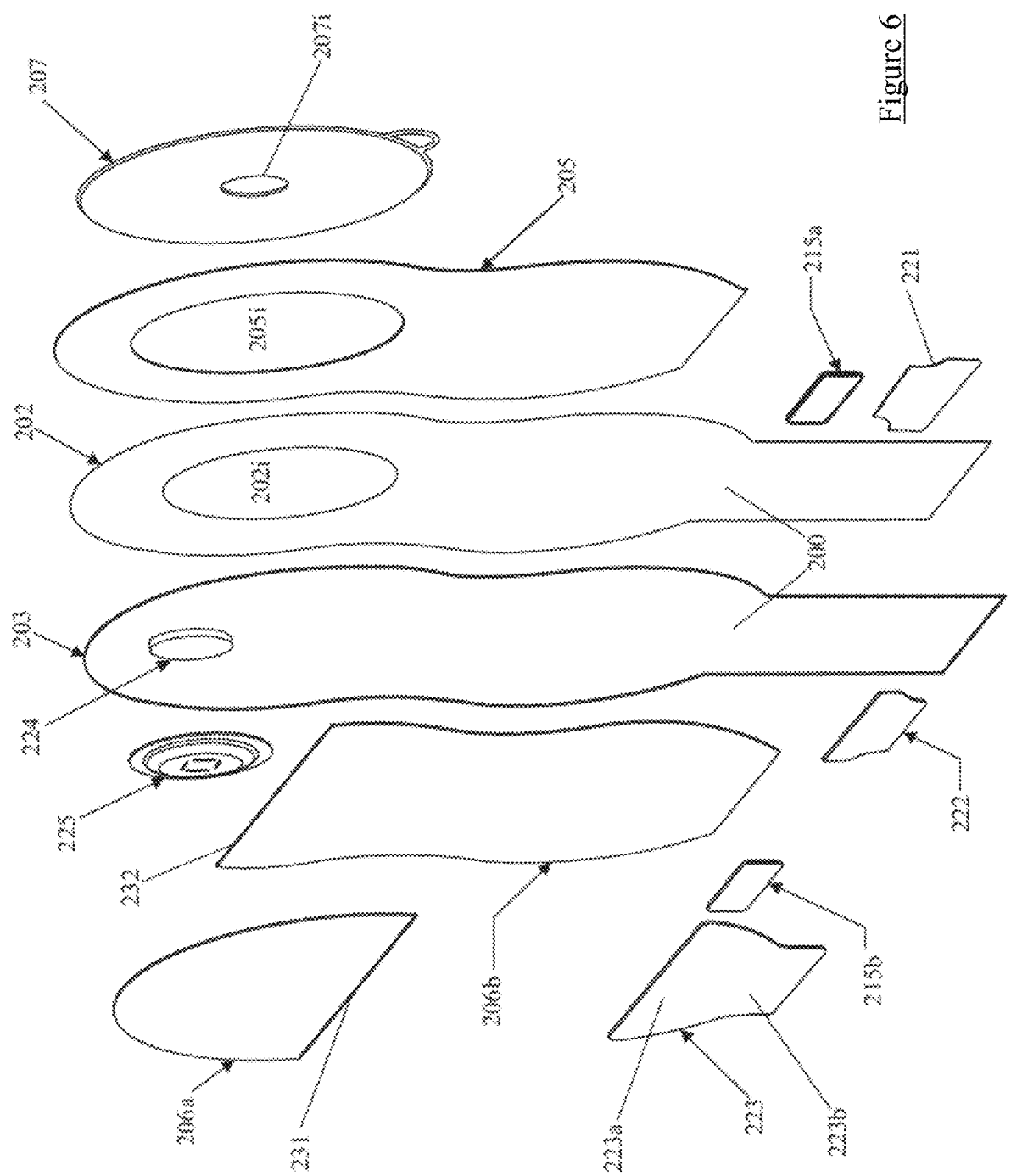

Referring to FIGS. 4 to 6, a further example of an ostomy pouch 201 according to the present invention is similar to that shown in FIGS. 1 to 3, with like features having similar reference numerals. The main difference is that the lower section 211 of the further example is shaped to accommodate/form a foldable drain. Thus, in contrast to the examples described above, this example of the ostomy pouch 201 is an open pouch that does not comprise a sealed perimeter.

Moreover, in this example, no separation wall is provided between the front 203 and rear 202 walls, and as such the cavity is not divided into two sections. The rear wall 202 features a large opening 202i in register with the stomal inlet 207i of the wafer 207 (which is connected to the rear wall 202 in the region between the periphery of the opening 202i and the periphery of the wafer, such that stomal output enters the cavity via the stomal inlet of the wafer and the opening 202i in the rear wall. The rear comfort layer 205 also features an opening 205i slightly larger than the opening 202i in the rear wall 202 and in register with it, so as to be sandwiched between the outermost edge of the wafer and the rear wall 202. The stomal inlet 207i is adjustable to fit the stoma of the ostomate.

In a similar fashion to the first example, the front comfort layer 206 of this example is formed of two parts: an upper part 206a; and a lower part 206b. The upper part 206a overlaps the lower part 206b across the majority of the width of the pouch 201 at a point on its height in register with the stomal inlet 207i. The overlap being defined by the lower edge 231 of the upper part 206a that overlaps the upper edge 232 of the lower part 206b.

In this example, there is also an optional gas filter 224 positioned in the front wall 203 at a height above the stomal inlet 207i to allow gas to exit the pouch 201. in this example, the filter 224 is covered by an optional filter cover patch 225 (not shown in FIG. 5) on the outside surface of the front wall 203. As such, the filter 224 and filter cover patch 225 are covered by the upper part 206a of the front comfort layer 206.

In this example, the drain extends from the lower edge of the ostomy pouch 201 such that the pouch 201 has a length, L, of 290 mm when the drain is in an unfolded configuration. In other examples, the length may be a different size, for example in the range 250 mm to 300 mm.

In this example, the lower section 211 comprises a drain aperture 40. The drain aperture 40 is an unsealed portion of the perimeter of the ostomy pouch 201 where the rear 202 and front 203 walls are not sealed.

In this example, the lower section 211 comprises a rounded portion 211a and a substantially rectangular drain portion 41 that accommodates the drain aperture 40, with the rounded portion 211a being adjacent the waisted section 212 and the drain portion 41 being distal the waisted section 212. The drain portion 41 is foldable along its length between an unfolded and a folded configuration as described later.

In this example, the lower section 211 comprises a continuous left edge 42 that extends from the left edge 213c of the waisted section 212 to a left vertex 44 of the drain aperture 40 around the curved left edge 42c of the generally rounded portion 211a and along a left edge 42d of the drain portion 41. Similarly, a continuous right-hand edge 43 extends from the right edge 214c of the waisted section 212 to a right vertex 45 of the drain aperture 40 around a continuously curved right edge 43c of the generally rounded portion 211a and along a right edge 43d of the drain portion 41. (Note that as FIG. 4 is a front view, the left edges of the pouch 1 are on the right of the figure and right edges of the pouch 1 on the left of the figure.)

In this example, the curved left 42c and right edges 43c of the generally rounded portion 211a have convex curvature. The radius of curvature, r3, is similar to the radius of curvature r2 as described for the ostomy pouch shown in FIGS. 1 to 3. The left 42d and right 43d edges of the drain portion 41 are parallel to one another along the majority of their length.

In this example, a single continuous edge seal 208 extends around the perimeter of the pouch 201 from the left vertex 44 of the drain aperture 40 to the right vertex 45 of the drain aperture 40, leaving the distal end of the drain aperture 40 open.

In this example, the drain portion 41 defines an elongate drain passage that extends from the cavity of the ostomy pouch 201 to the drain aperture 40 located at a lower end of the drain portion 41. The drain portion 41 is integral with the lower section 211 and as such, the rear wall 202 and the front wall 203 may each be a single piece of material that includes the upper section 210, the waisted section 212 and lower section 211 (including the drain portion 41). However, in this example, the rear comfort layer 205 and front comfort layer 206 do not cover the drain portion 41 of the rear wall 202 and the front wall 203.

In this example, communication between the cavity and the elongate drain passage is via a drain inlet 200 defined as the point of transition between the cavity and the drain portion 41. The drain inlet 200 allows passage of stomal output from the cavity into the drain portion 41 when the drain portion 41 is unfolded.

In this example, movement of the drain portion 41 between its unfolded or folded configuration opens or closes the drain aperture 40. This either permits or prevents outflow of the stomal output stored in the ostomy pouch 1 cavity.

In this example, the drain portion 41 can be repeatedly folded in the same sense along its length into a plurality of segments having approximately equal segment lengths and separated by folds. The drain portion 41 may therefore be successively folded one or more times such that the segments overlie each other. Each fold is formed across the width of the drain portion 41 and acts to inhibit and preferably prevent passage of stomal output out of the drain aperture 40.

In this example, first 221 and second 222 pursing strips are provided on the drain portion 41. The pursing strips 221, 222 provide both localised rigidity to the drain portion 41 and also define the locations and orientations of the segments and folds of the drain portion 41. The pursing strips 221, 222 comprise strips of flexible material attached drain portion 41, wherein the strips 221, 222 have a higher rigidity than the material of the drain portion 41. The pursing strips 221, 222 also have some resilience such that once attached to the drain portion 41, the pursing strips 221, 222 can each be squeezed laterally to arch the pursing strip and thereby open the elongate drain passage. In other examples, two or more pursing strips may be used.

In this example, the pursing strips 221, 222 are formed from polystyrene, but other examples may comprise any suitable material.

In this example, the first pursing strip 221 is attached to the rear wall 202 of the drain portion 41 adjacent the drain aperture 40. The second pursing strip 222 is attached to the front wall 203 of the drain portion 41 above the second strip 222. A longitudinal gap is provided between an upper edge of the first pursing strip 221 and a lower edge of the second pursing strip 222. The longitudinal gap therefore defines the location of a first fold of the drain portion 41. Each pursing strips 221, 222 spans the width of the drain portion 41 and extends the same distance along a length of the drain portion 41.

In this example, a rear fastening element 215a is arranged on the rear wall 202 and a front fastening element 215b is arranged on a flap 223 that is mounted to the front comfort layer 206. In this example of a two-part front comfort layer 206, the flap 223 is mounted to the lower part 206b of the comfort layer 206. The rear fastening element 215a and the front fastening element 215b comprise corresponding hook-and-loop type fastener elements. The rear fastening element 215a is located on the drain portion 41 above the second pursing strip 222. A longitudinal gap is provided between an upper edge of the second pursing strip 222 and a lower edge of the rear fastening element 215a. The longitudinal gap therefore defines the location of a second fold of the drain portion 41.

In this example, the flap 223 comprises a first flange 223a and a second flange 223b formed of one integral piece. The first flange 223a spans substantially all of the width of the lower rounded section 211a, but does not extend over the edge seal 208, at a point one third up the length of the rounded section 211a from the drain inlet 200. The first flange 223a is attached to the comfort material 206 by a single weld that spans substantially its entire width. This weld is made possible by the web of hot-melt adhesive 51 which coats the inside surface of the woven material 50 that the comfort material 206 is made from, which, when heated to a sufficient temperature (for sufficiently long and under sufficiently high pressure), fully penetrates the woven material to bond with the material of the flap 223. The second flange 223b extends from the lower edge of the first flange 223a and is connected to the pouch 1 only by the first flange 223a. The second flange 223b is contoured so as to conform to the shape of the rounded portion 211a but is thinner, tracing the inside edge of the peripheral weld 208. As such, the second flange 223b extends downwards from the first flange 223a within the perimeter defined by the edge seal 208 of the pouch 201.

In this example, the flap 223 has an outside surface, facing away from the ostomate in use and an opposite inside surface. The front fastening element 215b is located on the inside surface of the second flange 223b at a position above the rear fastening element 215a. A longitudinal gap is provided between an upper edge of the rear fastening element 215a and a lower edge of the front fastening element 215b and defines the location of a third fold of the drain portion 41. The flap 223 is formed from a flexible sheet material that is more rigid than the flexible sheet material of the rear wall 202, front wall 203 and comfort layers 205, 206. In this example, the flap 223 is formed from a plastic foam which provides a desirable rigidity.

In an alternative, otherwise identical, example, the flap 223 is formed of the same hot-melt coated woven comfort material as the comfort layer 206. Whilst this material is not as rigid as a plastic foam material, it is desirable aesthetically, as it matches with the remainder of the comfort layer, making the fact that the pouch is drainable less obvious.

Folding of the drain portion 41 may be carried out as follows. First, the distal end of the drain portion 41 is folded upwards and away from the rear of the ostomy pouch 201 about the first fold line to locate the first pursing strip 221 over the second pursing strip 222. Secondly, the drain portion 41 and the pursing strips 221, 222 are folded again, in the same sense, about the second fold line and then the third fold line such that the folded and stacked first pursing strip 221, second pursing strip 222 and first fastening element 215*a* are located beneath the second flange 223*b* of the flap 223 with the rear fastening element 215*a* being exposed and adjacent the front fastening element 215*b*. Finally, the second flange 223*b* of the flap 223 is pressed onto the folded drain portion to secure together the rear fastening element 215*a* and the front fastening element 215*b*.

In these examples, the drain portion 41 can then be unfolded by reversing the above procedure.

FIG. 4*b* shows an alternative arrangement of the flap shown in FIGS. 4*a*, 5 and 6. In most regards the pouches are identical, with the same numbers referring to the same features, however in this example, a flap 240 may be integrally provided as a part of the front comfort layer 206. That is the lower part of the front comfort material 206*a* covers the drain portion 41 when the drain is in the retracted position. The lower part of the front comfort layer 206*a* extends to the lower edge of the pouch and the lower edge 243 is curved so as to mimic the lower edge of a non-drainable ostomy pouch such as in the example in FIGS. 1-3. To form the flap 240 the edge join for the lower part of the front comfort layer 206*a* does not extend around the entire perimeter of the pouch, instead it terminates 241*a*,241*b* approximately at the midpoint of the lower portion 211*a*. This allows the flap 240 to be folded about a fold line 243 defined as a line between the two points 241*a*,241*b* where the edge join terminates. The edge join can be positioned such that the fold line is above the retracted drain allowing access to the drain when the flap is open. The drain otherwise functions in the same way as the example with a separate flap.

As in the first example, in the both alternatives of the second example, the rear comfort layer 205 and the front comfort layer 206 are formed of a flexible sheet material comprised of a woven fabric layer 50 with a web of hot-melt adhesive 51 coated on one surface—its inside surface in use (see FIG. 7). In this example, the fabric layer 50 is forms the outside surface of the rear 205 and front 206 comfort layers respectively, with the web of hot-melt adhesive 51 disposed on the corresponding inside surfaces, facing the rear 202 and front 203 walls. Other example may comprise additional fabric layers and/or adhesive layers as required. In this example, the woven fabric layer comprises polyester but in other example any one or more of nylon, viscose, polyethylene and polypropylene could be used in addition or as an alternative.

In this example, the woven fabric layer has an area density of 58 g/m$^2$, a tensile strength of 280 to 300 N, and a tear strength of 18 N. Other example may have different compositions, for example an area density of 50 to 70 g/m$^2$, a tensile strength of 200 to 400 N, and a tear strength of 10 to 30 N. Some examples may also have a colour fastness to any one or more of rubbing, perspiration or washing (40°) of 4 to 5, and an abrasion of >50,000. Certain examples also comprise a woven polyester with a water repellent finish. The water repellent finish may be fluorocarbon based and may be dyed heat set or boil off heat set. A suitable woven polyester layer is available from Newton Textiles Limited of Northamptonshire, UK, under the 75DCWR Designation, such as 75DCWRWHITE (for a white variant).

In this example, the hot-melt adhesive comprises ethylene-vinyl acetate (EVA).

In another example the hot-melt adhesive is a polyolefin.

In another example the hot-melt adhesive is polyurethane.

In another example the hot-melt adhesive is polyvinylidene chloride (PVDC).

In another example the hot-melt adhesive is silicon rubber.

In another example the hot-melt adhesive is a fluoropolymer.

In another example the hot-melt adhesive is polycarbonate.

In another example the hot-melt adhesive is styrene block co-polymer.

In another example the hot-melt adhesive is polyester.

In another example the hot-melt adhesive is polyamide.

In another example the hot-melt adhesive is polycaprolactone.

In this example, the web of hot-melt adhesive has an area density of 25 g/m$^2$. A suitable EVA hot-melt adhesive is available from Protechnic SA of Cernay, France, under the designation 3Z8 and described by Protechnic SA as a web, but other hot-melts, such a co-polyester hotmelt web were evaluated successfully.

In this example, the hot-melt adhesive is once again coated onto the fabric layer over an entire area of the rear 205 and the front 206 comfort layers. In other examples, the hot-melt adhesive may be coated to part of area of the rear 205 and front 206 comfort layers, or specific regions thereof. As mentioned above, where the web is formed, as shown in FIG. 7, it includes a mass M of hot-melt adhesive with numerous voids V therein, where there is an absence (or substantial absence, possibly including a trace) of hot-melt adhesive, thus it takes the general form of a lattice, mesh or grid. As can be seen, in this example the voids are irregularly shaped and spaced and a relatively smaller area is covered by the mass than that which is free of adhesive in the voids. In other examples (not shown) the voids could be regularly shaped and/or regularly spaced.

Advantageously, the use of the hot melt adhesive allows both comfort layers 205, 206 to be joined to the rear wall 2 and front wall 3 without the need for specialist intervening layers or the application of adhesive during the construction process and with adhesion even in regions where woven layers are joined to each other (i.e. the overlap) or to other materials that would not normally weld to a woven layer (such as the flap 223). In this example, the peripheral weld defined by the edge seal 208 is formed by a plurality of joins, a first join joining the rear comfort layer 205 to the rear wall 202 and the front wall 203 and a second join joining the front comfort layer 206 to the other three layers in a subsequent joining step. In other the front comfort layer 206 to, various welds may be used as required or desired. For example, the weld may only correspond to a portion of the weld joining the rear 202 and front 203 walls. The weld attaching the rear comfort layer 205 to the rear wall 202 may be the same as the weld attaching the front comfort layer 206 to the front wall 203, but performed subsequently to the weld which joins the rear 2 and front 3 walls. As set out before, the hot-melt adhesive 51 protects the fabric layers 50 from undesirable fraying.

Methods of Forming Ostomy Pouches

Referring to FIG. 8 an apparatus 300 for use in a method of forming ostomy pouches according to the present invention is shown schematically. In this embodiment, the apparatus 300 comprises four rollers 301, 302, 303 and 304, a first stamp welding machine 305, a second stamp welding machine 306 and a cutting machine 307. The rollers 301, 302, 303 and 304 are used to advance a first 311, second 312, third 313 and fourth 314 flexible sheet materials respectively in the direction of the arrow D. For simplicity, additional rollers used to advance and guide the sheets are not shown.

In this embodiment, the apparatus 300 is configured to construct an ostomy pouch 1,201 as described above, comprising a first, front, cavity wall 3; a second, rear, cavity wall 2; a first, front, comfort layer 6; and a second, rear, comfort layer 5. It will be appreciated that the process shown is simplified, with features such as the wafer and stomal inlet not shown, however the methods by which these could be provided (for example cutting an opening and gluing in a wafer) will be well known to those skilled in the art.

The first 311 and second 312 sheets of material are plastics film used for the first, front, cavity wall 3 and second, rear, cavity wall 2 of the pouch respectively. As such, the material used for these sheets is the same. In some embodiments the plastics films may be different, for example the rear cavity wall may use an opaque material whereas the front cavity wall may be transparent to allow for inspection. In further embodiments the front and rear walls of the cavity may be formed from the same sheet of plastics film, which may be folded over to provide the two walls. The plastics films of this embodiment correspond to the plastic films that are described above.

The third 313 and fourth 314 sheets of material are used for the front 6 and rear 5 comfort layers of the pouch respectively. As described above, the material used for the comfort layers comprises a fabric layer 313a, 314a with a web of hot melt adhesive 313b, 314b applied thereto. The third 313 and fourth 314 sheets of material have been previously formed in a separate facility, days earlier, by a coating processing, such as roll-coating process, in which a thin sheet of EVA film is advanced from a roll and laminated under heat and pressure onto a sheet of fabric material similarly advanced from a roll. The EVA coated material is then cooled and rolled onto a new roll, on which it is delivered. The thinness of the EVA film combined with the heating during lamination causes the formation of voids V in the mass M of the EVA web 51 that is formed.

The first 311 and second 312 sheets of material are advanced from their respective rolls 301 and 302, the two sheets are brought together by rollers (not shown) such that they are in contact and advance at the same rate as one another. Next the fourth sheet 314 is advanced from its roller 304 and guided by rollers (not shown) such that it is adjacent to the second sheet 312. As can be seen in FIG. 8, the hot melt adhesive 314b (denoted by a dashed line) faces towards the second sheet 312 of material, such that the hot melt adhesive 314b is arranged adjacent the second sheet 312.

The first 311, second 312 and fourth 314 sheets of material, stacked in that order, advance at the same rate into the first stamp welding machine 305. The first stamp welding machine 305 comprises a heated die which applies a pressure of between 2.5 bar and 3 bar, such as 2.6-2.8 bar, in this particular example 2.7 bar, to the stacked sheets of material and heats them to between 100° C. and 150° C., such as 110-130° C., in this particular example 120° C., for a period of between 500 ms and 750 ms, in this particular example 500 ms, the die is shaped to correspond to the perimeter of the pouch to be made, in other embodiments further welds may be formed by the same die. Under the above conditions of pressure and temperature the two sheets 311, 312 of plastics film are welded together where the die is applied so as to form a sealed cavity. The weld is approximately 4 mm wide. In these conditions the EVA web 314b on the comfort layer 314 also becomes liquid, the liquid EVA permeates into the fabric material 314a of the second comfort layer 314 and bonds to the second sheet 312 of material securing the second comfort layer 314 to the second sheet 312 of material.

Due to the relatively higher temperatures and/or pressures required to weld the two plastics films 311,312 together as compared to the melting point to the EVA web 314b the EVA may leak so far through the fabric layer as to become visible, and potentially become discoloured due to the heat of the die, although these are reduced as compared to methods where the pouch is formed by a single welding step where the temperature, pressure and/or time period are greater still, in order to provide adequate conditions at the join between the cavity walls, despite the intervening layers damping the pressure, and insulating against or at least slowing the passage of heat. In some embodiments this EVA leakage may be at least partially reduced or obviated by arranging the die such that it contacts the first sheet 311 of plastics film on the opposite side of the stacked sheets.

In some embodiments the first stamp welding machine 305 comprises a further die which is arranged on the opposing side of the stacked sheets to the first die. The further die may also be heated, optionally at a different temperature to the first die.

The now welded first 311, second 312, and fourth 314 sheets advance out of the first stamp welding machine 305. The third sheet 313 of material, which forms the front comfort layer 6, is advanced from the third roller 303 at the same rate as the welded first 311, second 312 and fourth 314 sheets, and is directed by rollers (not shown) such that it is adjacent to the first sheet 311. As can be seen in FIG. 8, the hot melt adhesive 313b (denoted by a dashed line) faces towards the first sheet 311 of material, such that the hot melt adhesive 313b is arranged adjacent the first sheet 311.

The first 311, second 312, third 313 and fourth 314 sheets of material then advance at the same rate into a second stamp welding machine 306. The second stamp welding machine 306 comprises a second heated die which applies a pressure of between 2.5 bar and 3 bar, such as 2.6-2.8 bar, in this particular example 2.7 bar, to the stacked sheets of material and heats them to between 130° C. and 160° C., preferably between 140° C. and 150° C. and in this particular example 145° C. for a period of between 500 ms and 750 ms, in this particular example 500 ms, the die is shaped to correspond to the perimeter of the pouch to be made. The timing of the second heated die and the repetition rate are set such that the second heated die is applied to the same areas of the advancing sheets of material as the first heated die—that is the bond produced by the second stamp welding machine 306 overlaps the join formed by the first stamp welding machine 305.

In another embodiment the second heated die applies a pressure of between 2.5 bar and 3 bar, such as 2.6-2.8 bar, in this particular example. 2.7 bar, to the stacked sheets of material and heats them to between 90° C. and 140° C., preferably between 100° C. and 120° C. and in this particular example 110° C. for a period of between 500 ms and 750 ms, in this particular example 500 ms. In this embodiment the temperature and pressure applied by the second heated die is less than that applied by the first heated die. This is possible because the plastics films which form the cavity, and require a higher temperature to weld, are already bonded, the second heated die need only melt the hot melt adhesive to a sufficient extent that bonding of the first comfort layer 313 to the other layers is possible, it does not need to be sufficient to also allow the plastics films to join. The temperature, pressure, and time parameters of the second heated die are selected such that the hot melt adhesive 313b does not leak through the fabric layer 313a, and thus is not visible. As the first, front, comfort layer 6 is visible when the pouch is worn by a user, the avoidance of visible EVA is of greater importance on this side than on the second, rear, comfort layer 5 as this is not visible as it faces the user's body.

As will be readily understood by those skilled in the art, the range of suitable, and optimal values of temperature, pressure, and time parameters of the first 305 and second 306 stamp welding machines will vary depending upon a number of factors including the materials used for the cavity walls, the comfort layers and the hot melt adhesive. Different hot melt adhesives will have different melting points and different viscosity-temperature dependencies, this will affect the rate at which the hot melt adhesive "flows" through and penetrates the fabric of the comfort layer. For example, a more viscous hot melt adhesive may require less time to sufficiently flow into the fabric layer to a sufficient extent to provide a sufficiently strong join and be of increased risk of leaking through the fabric layer completely and becoming visible or require less pressure to be applied by the die to achieve the same penetration. However, if the temperature applied to the same hot melt adhesive was reduced, the viscosity would reduce correspondingly, thereby increasing the time required the allow for a sufficiently strong bond whilst also reducing the chance of the hot melt adhesive becoming visible.

Likewise, the choice of material for the comfort layer will affect the rate at which the hot melt adhesive "flows". For example, thinner or more porous comfort layer materials will require the temperature and pressure to be applied for a shorter time period and/or less viscous hot melt adhesives to achieve sufficient penetration and ensure the hot melt adhesive does not become visible. Likewise, a thicker or less porous comfort layer materials will allow higher temperatures and/or pressures to be applied for longer periods without the hot melt adhesive becoming visible.

Those skilled in the art will readily be able to adjust the temperature, pressure, and application time period of the second stamp welding press 306 such that the hot melt adhesive provides a sufficiently strong join without leaking through the comfort material and thus becoming visible.

Similarly, those skilled in the art will be able to adjust the temperature, pressure and application time period of the first stamp welding press 305 to ensure that the weld between the two cavity walls is securely sealed, whilst also minimising the leakage of hot melt adhesive through the rear comfort layer.

In addition to the improved aesthetics of the two-step process when the parameters of both steps have been optimised for the specific materials, the use of a two-step process in and of itself provides an improvement; the conditions applied by the first 305 and second 306 stamp welding machines are less harsh than those that would be applied by a stamp welding machine that was joining the both comfort layers and welding the cavity walls in a single step.

For example, in order to produce the same ostomy pouch, with the same materials, would require a temperature of between 150° C. and 180° C. with a pressure of between 1.4 and 2.7 bar for a time period of between 1 and 1.2 seconds. These harsher conditions, in particular the endurance of the conditions for substantially longer to allow adequate heat transfer to the cavity walls would be more likely to cause discolouration of the comfort layer(s).

In some embodiments the second stamp welding machine 306 comprises a further die which is arranged on the opposing side of the stacked sheets to the second die. The further die may also be heated, optionally at a different temperature to the second die.

Once the first comfort layer 313 has been joined to the remainder of the pouch, the combined sheets 311,312,313 and 314 can proceed from the second stamp welding press 306 to the cutting machine 307. The cutting machine 307 cuts around the perimeter of the sealed weld line created by the first 305 and second 306 stamping machines. This frees each ostomy pouch from the advancing sheets from where they can either be collected or progress further of the assembly line to assemble further components. In some embodiments the cutting free of the ostomy pouches could occur simultaneously with the second welding step.

Figure 9:
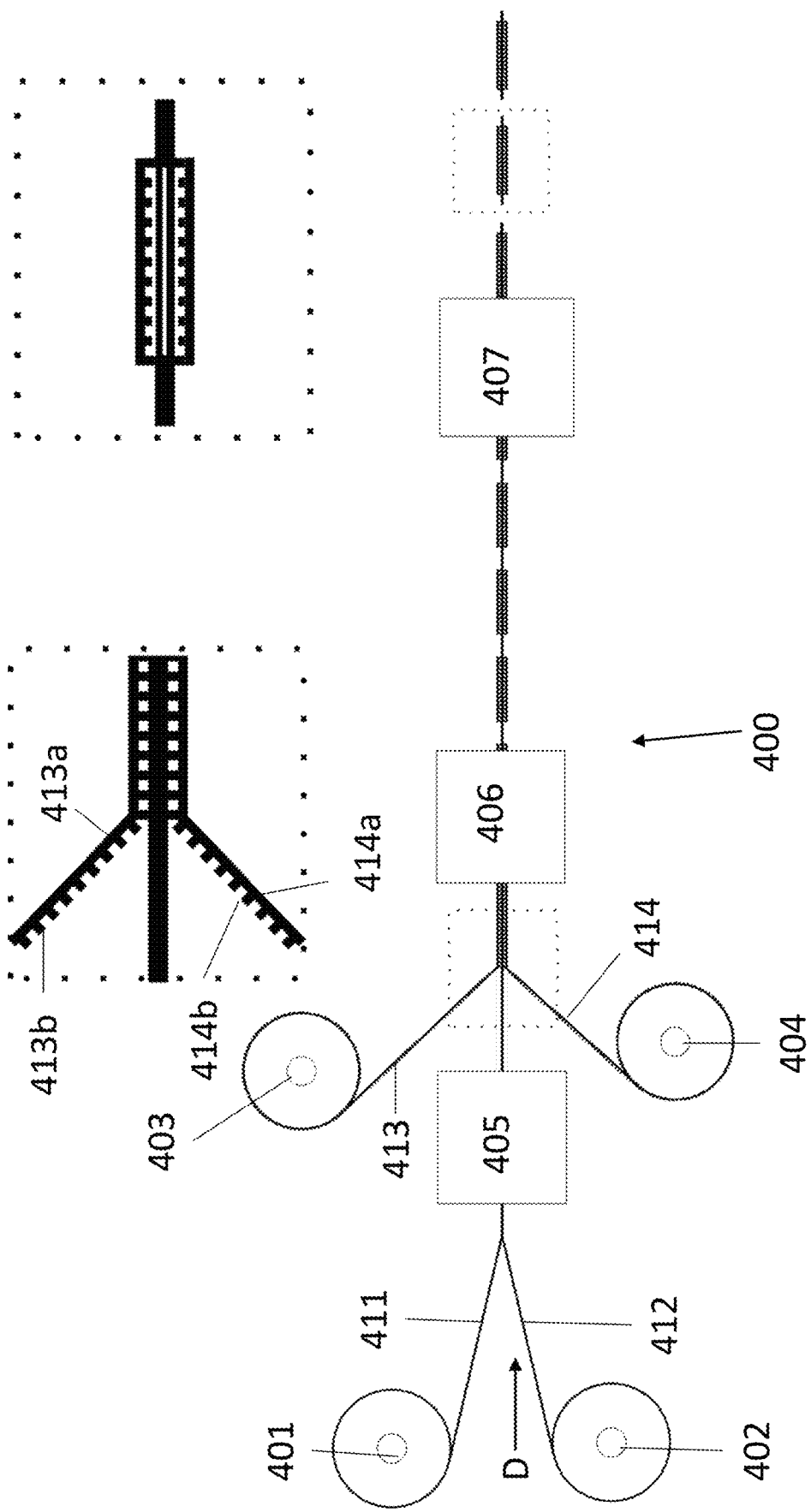
FIG. 9 is a side view of an alternative apparatus for producing an ostomy pouch according to the present invention.

Referring to FIG. 9 another apparatus 400 for use in a method of forming ostomy pouches according to the present invention is shown schematically. The apparatus is similar to that described above with like features sharing the same numbering advanced by 100.

The apparatus 400 comprises four rollers 401, 402, 403 and 404, a first stamp welding machine 405, a second stamp welding machine 406 and a cutting machine 407. The rollers 401, 402, 403 and 404 are used to advance a first 411, second 412, third 413 and fourth 414 flexible sheet material respectively in the direction of the arrow D. For simplicity, additional rollers used to advance and guide the sheets are not shown.

As in the previous example the first 411 and second 412 sheets of material are plastics film used for the first, front, cavity wall 3 and second, rear, cavity wall 2 of the pouch respectively, and could, in alternative embodiments be provided in a single sheet.

The third 413 and fourth 414 sheets of material are used for the front 6 and rear 5 comfort layers of the pouch respectively. The comfort layers comprise a fabric layer 413*a*, 414*a* with a web W of hot melt adhesive 413*b*, 414*b* applied thereto. Again, the third 413 and fourth 414 sheets of material have been previously formed in a separate facility as described above.

Similarly to the previous apparatus, the first 411 and second 412 sheets of material are advanced from their respective rollers 401 and 402, the two sheets are brought together by rollers (not shown) such that they are in contact and advance at the same rate as one another. However unlike in the previous embodiment, a sheet of comfort material is not provided at this time, instead the first 411 and second 412 sheets of material advance into the first stamp welding machine 405.

The first stamp welding machine 405 comprises a heated die which applies a pressure of between 2.5 bar and 3 bar, such as 2.6-2.8 bar, in this particular example. 2.7 bar, to the stacked sheets of material and heats them to between 100° C. and 150° C., such as 110-130° C., in this particular example. 120° C., for a period of between 500 ms and 750 ms, in this particular example 500 ms, the die is shaped to correspond to the perimeter of the pouch to be made, in other embodiments further welds may be formed by the same die. Under the conditions of pressure and temperature the two sheets 411, 412 of plastics film weld together where the die is applied so as to form a sealed cavity. The weld is approximately 4 mm wide.

In some embodiments the first stamp welding machine 405 comprises a further die which is arranged on the opposing side of the stacked sheets to the first die. The further die may also be heated, optionally at a different temperature to the first die.

The now welded first 411 and second 412 sheets advance out of the first stamp welding machine 405. The third 413 and fourth 414 sheets of material, the first comfort layer and second comfort layer respectively, are advanced from the third 403 and fourth 404 rollers at the same rate as the welded first 411 and second 412 sheets and are directed by rollers (not shown) such that they are adjacent to the first sheet 411 and second sheet 412 respectively. As can be seen in FIG. 9, the hot melt adhesive 413b, 414b (denoted by a dashed line) face each other, such that the hot melt adhesive 413b,414b is arranged adjacent the plastics film sheet. Although FIG. 9 shows the third 413 and fourth 414 sheets of material being arranged simultaneously, they could of course be arranged consecutively.

The first 411, second 412, third 413 and fourth 414 sheets of material then advance at the same rate into a second stamp welding machine 406. The second stamp welding machine 406 comprises a second heated die which applies a pressure of between 2.5 bar and 3 bar, such as 2.6-2.8 bar, in this particular example. 2.7 bar, to the stacked sheets of material and heats them to between 130° C. and 160° C., preferably between 140° C. and 150° C. and in this particular example 145° C. for a period of between 500 ms and 750 ms, in this particular example 500 ms, the die is shaped to correspond to the perimeter of the pouch to be made.

The timing of the second heated die and the repetition rate are set such that the second heated die is applied to the same areas of the sheets of material as the first heated die—that is the bond produced by the second stamp welding machine 406 overlaps the join formed by the first stamp welding machine 405.

In another embodiment the second heated die applies a pressure of between 2.5 bar and 3 bar, such as 2.6-2.8 bar, in this particular example. 2.7 bar, to the stacked sheets of material and heats them to between 90° C. and 140° C., preferably between 100° C. and 120° C. and in this particular example 110° C. for a period of between 500 ms and 750 ms, in this particular example 500 ms. In this embodiment the temperature and pressure applied by the second heated die is less than that applied by the first heated die. This is possible because the plastics films which form the cavity, and require a higher temperature to weld, are already bonded, the second heated die need only melt the hot melt adhesive to a sufficient extent that bonding of the first 413 and second 414 comfort layers to the film layers 411,412 is possible, it does not need to be sufficient to allow the plastics films to join (the welding temperature and pressure of the plastics films will be higher than that required to adhere the hot melt adhesive). The temperature, pressure, and time parameters of the second heated die can be selected such that the hot melt adhesive 413b,414b does not leak through the fabric layer 413a,414a and thus is not visible.

As outlined above, those skilled in the art will readily be able to adjust the temperature, pressure, and application time of the second stamp welding press 406 such that the hot melt adhesive provides a sufficiently strong join without leaking through the comfort material and thus becoming visible.

In some embodiments the second stamp welding machine 406 comprises a further die which is arranged on the opposing side of the stacked sheets to the second die. The further die may also be heated, optionally at a different temperature to the second die.

Once the first 413 and second 414 comfort layers have been joined to the remainder of the pouch, the combined sheets 411,412,413 and 414 can proceed from the second stamp welding press 406 to the cutting machine 407. The cutting machine 407 cuts around the perimeter of the sealed weld line created by the first 405 and second 406 stamping machines. This frees each ostomy pouch from the advancing sheets from where they can either be collected or progress further of the assembly line to assemble further components. In some embodiments the cutting free of the ostomy pouches could occur simultaneously with the second welding step.

Figure 10:
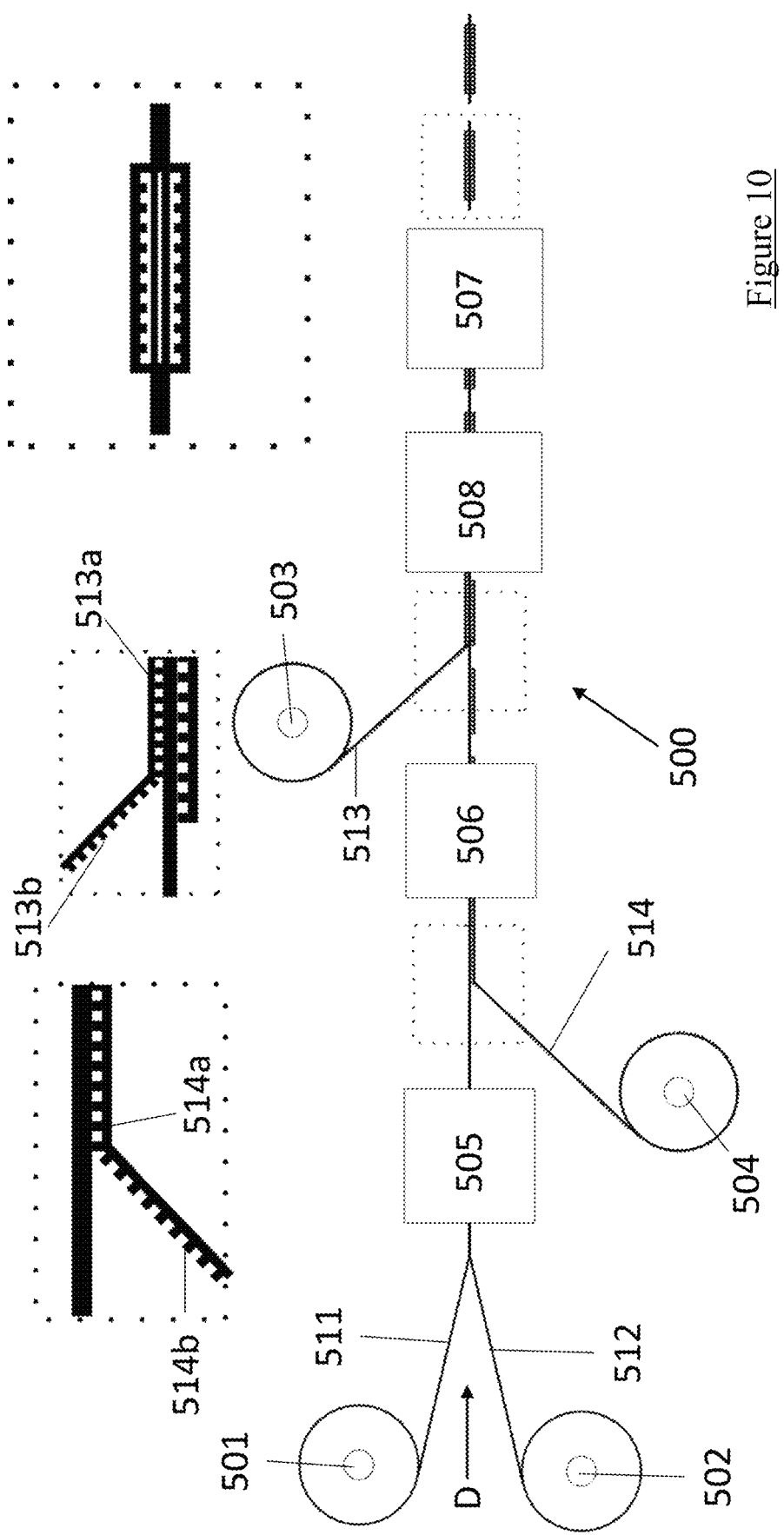
FIG. 10 is a side view of a further apparatus for producing an ostomy pouch according to the present invention.

Referring to FIG. 10 another apparatus 500 for use in a method of forming ostomy pouches according to the present invention is shown schematically. The apparatus is similar to that described with respect to the two previous apparatuses with like features sharing the same numbering advanced by 200 and 100 respectively.

The apparatus 500 comprises four rollers 501, 502, 503 and 504, a first stamp welding machine 505, a second stamp welding machine 506, a third stamp welding machine 508 and a cutting machine 507. The rollers 501, 502, 503 and 504 are used to advance a first 511, second 512, third 513 and fourth 514 flexible sheet material respectively in the direction of the arrow D. For simplicity, additional rollers used to advance and guide the sheets are not shown.

As in the previous example the first 511 and second 512 sheets of material are plastics film used for the first, front, cavity wall 3 and second, rear, cavity wall 2 of the pouch respectively, and could, in alternative embodiments be provided in a single sheet.

The third 513 and fourth 514 sheets of material are used for the front 6 and rear 5 comfort layers of the pouch respectively. The comfort layers comprise a fabric layer 513a, 514a with a web of hot melt adhesive 513b, 514b applied thereto. Again, the third 513 and fourth 514 sheets of material have been previously formed in a separate facility as described above.

Similarly to the previous apparatus, the first 511 and second 512 sheets of material are advanced from their respective rollers 501 and 502, the two sheets are brought together by rollers (not shown) such that they are in contact and advance at the same rate as one another. However unlike in the first embodiment, a sheet of comfort material is not provided at this time, instead the first 511 and second 512 sheets of material advance into the first stamp welding machine 505.

The first stamp welding machine 305 comprises a heated die which applies a pressure of between 2.5 bar and 3 bar, such as 2.6-2.8 bar, in this particular example. 2.7 bar, to the stacked sheets of material and heats them to between 100° C. and 150° C., such as 110-130° C., in this example 120° C., for a period of between 500 ms and 750 ms, in this example 500 ms, the die is shaped to correspond to the perimeter of the pouch to be made. In other embodiments, further welds may be made by the first stamp welding machine 505. Under the conditions of pressure and temperature the two sheets 511, 512 of plastics film weld together where the die is applied so as to form a sealed cavity. The weld is approximately 4 mm wide.

In some embodiments the first stamp welding machine comprises a further die which is arranged on the opposing side of the stacked sheets to the first die. The further die may also be heated, optionally at a different temperature to the first die.

The now welded first 511 and second 512 sheets advance out of the first stamp welding machine 505. The fourth 514 sheet of material, the second comfort layer is advanced from the fourth 504 roller at the same rate as the welded first 511 and second 512 sheets and is directed by rollers (not shown) such that it is adjacent to the second sheet 512. As can be seen in FIG. 10, the hot melt adhesive 514b (denoted by a dashed line) faces the second sheet 512, such that the hot melt adhesive 514b is arranged adjacent to the plastics film sheet.

The first 511, second 512, and fourth 514 sheets of material then advance at the same rate into a second stamp welding machine 506, which comprises a second heated die which applies a pressure of between 2.5 bar and 3 bar, such as 2.6-2.8 bar, in this particular example. 2.7 bar, to the stacked sheets of material and heats them to between 130° C. and 160° C., preferably between 140° C. and 150° C. and in this particular example 145° C. for a period of between 500 ms and 750 ms, in this particular example 500 ms, the die is shaped to correspond to the perimeter of the pouch to be made. The timing of the second heated die and the repetition rate are set such that the second heated die is applied to the same areas of the advancing sheets of material as the first heated die—that is the bond produced by the second stamp welding machine 506 overlaps the join formed by the first stamp welding machine 505.

In another embodiment the second heated die applies a pressure of between 2.5 bar and 3 bar, such as 2.6-2.8 bar, in this particular example. 2.7 bar, to the stacked sheets of material and heats them to between 90° C. and 140° C., preferably between 100° C. and 120° C. and in this particular example 110° C. for a period of between 500 ms and 750 ms, in this particular example 500 ms. In this embodiment the temperature and pressure applied by the second heated die is less than that applied by the first heated die. This is possible because the plastics films which form the cavity, and require a higher temperature to weld, are already bonded, the second heated die need only melt the hot melt adhesive to a sufficient extent that bonding of the second 514 comfort layer to the film layer 512 is possible, it does not need to be sufficient to allow the plastics films to join (the welding temperature and pressure of the plastics films will be higher than that required to adhere the hot melt adhesive). The temperature, pressure, and time parameters of the second heated die can be selected such that the hot melt adhesive 514b does not leak through the fabric layer 514a and thus is not visible.

As outlined above, those skilled in the art will readily be able to adjust the temperature, pressure, and application time of the second stamp welding press 506 such that the hot melt adhesive provides a sufficiently strong join without leaking through the comfort material and thus becoming visible.

In some embodiments the second stamp welding machine 506 comprises a further die which is arranged on the opposing side of the stacked sheets to the second die. The further die may also be heated, optionally at a different temperature to the second die.

Once the second 514 comfort layer has been joined to the film sheets the combined sheets 511,512,514 can proceed from the second stamp welding press 506 to the third stamp welding press 508.

Prior to entering the third stamp welding press 508 the third sheet 513 of material is directed by rollers such that it is adjacent to the other three layers in a similar fashion as described for the fourth sheet 514, with the hot melt adhesive 513b arranged adjacent to the first sheet 511 of film.

The third stamp welding machine 308 comprises a third heated die which applies a pressure of between 2.5 bar and 3 bar, such as 2.6-2.8 bar, e.g. 2.7 bar, to the stacked sheets of material and heats them to between 130° C. and 160° C., preferably between 140° C. and 150° C. and more preferably 145° C. for a period of between 500 ms and 750 ms, preferably 500 ms, the die is shaped to correspond to the perimeter of the pouch to be made. The timing of the third heated die and the repetition rate are set such that the third heated die is applied to the same areas of the advancing sheets of material as the first and second heated die—that is the join produced by the third stamp welding machine 508 overlaps the join formed by the first 505 and second 506 stamp welding machines.

In another embodiment the third heated die may apply a pressure of between 2.5 bar and 3 bar, such as 2.6-2.8 bar, in this particular example. 2.7 bar, to the stacked sheets of material and heats them to between 90° C. and 140° C., preferably between 100° C. and 120° C. and in this particular example 110° C. for a period of between 500 ms and 750 ms, in this particular example 500 ms. In this embodiment the temperature and pressure applied by the third heated die is less than that applied by the first heated die. This is possible because the plastics films which form the cavity, and require a higher temperature to weld, are already bonded, the second heated die need only melt the hot melt adhesive to a sufficient extent that bonding of the first 513 comfort layer to the first film layer 511 is possible, it does not need to be sufficient to allow the plastics films to join (the welding temperature and pressure of the plastics films will be higher than that required to adhere the hot melt adhesive). The temperature, pressure, and time parameters of the third heated die can be selected such that the hot melt adhesive 513b does not leak through the fabric layer 513a and thus is not visible.

As outlined above, those skilled in the art will readily be able to adjust the temperature, pressure, and application time of the third stamp welding press 508 such that the hot melt adhesive provides a sufficiently strong join without leaking through the comfort material and thus becoming visible.

In some embodiments the third stamp welding machine 508 comprises a further die which is arranged on the opposing side of the stacked sheets to the third die. The further die may also be heated, optionally at a different temperature to the third die.

Once the first comfort layer 513 is joined in the joined sheets 511,512,513,514 advance to the cutting machine 507. The cutting machine cuts around the perimeter of the sealed weld line created by the first, second and third stamping machines 505,506,508. This frees each ostomy pouch from the advancing sheets where they can either be collected or progress further of the assembly line to assemble further components. In some embodiments the cutting free of the ostomy pouches could occur simultaneously with the second welding step.

EXAMPLES

As described in the above embodiments, the conditions applied by the first stamp welding machine 305,405,505, the second stamp welding machine 306,406,506 can be varied depending upon the materials used for the cavity walls, the comfort layers and the choice of hot melt adhesive. The main point of the invention is that by using a (minimum) two-step joining process, conditions of each step can be less harsh and avoid damage or defects in appearance of the pouch, especially the comfort layer thereof. It is particularly preferred, but not essential that the conditions of the second step are less harsh than the first step. Accordingly, the following table sets out examples of the first temperature ($T_1$), first pressure ($P_1$) and first time period ($t_1$) relative to the second temperature ($T_2$), second pressure ($P_2$) and second time period ($t_2$) respectively.

| Example | T | $P_1$ | $t_1$ |
| --- | --- | --- | --- |
| 1 | Greater than $T_2$ | Greater than $P_2$ | Greater than $t_2$ |
| 2 | Greater than $T_2$ | Greater than $P_2$ | Less than $t_2$ |

-continued

| Example | T | $P_1$ | $t_1$ |
|---|---|---|---|
| 3 | Greater than $T_2$ | Greater than $P_2$ | Equal to $t_2$ |
| 4 | Greater than $T_2$ | Less than $P_2$ | Greater than $t_2$ |
| 5 | Greater than $T_2$ | Less than $P_2$ | Less than $t_2$ |
| 6 | Greater than $T_2$ | Less than $P_2$ | Equal to $t_2$ |
| 7 | Greater than $T_2$ | Equal to $P_2$ | Greater than $t_2$ |
| 8 | Greater than $T_2$ | Equal to $P_2$ | Less than $t_2$ |
| 9 | Greater than $T_2$ | Equal to $P_2$ | Equal to $t_2$ |
| 10 | Less than $T_2$ | Greater than $P_2$ | Greater than $t_2$ |
| 11 | Less than $T_2$ | Greater than $P_2$ | Less than $t_2$ |
| 12 | Less than $T_2$ | Greater than $P_2$ | Equal to $t_2$ |
| 13 | Less than $T_2$ | Less than $P_2$ | Greater than $t_2$ |
| 14 | Less than $T_2$ | Equal to $P_2$ | Greater than $t_2$ |
| 15 | Equal to $T_2$ | Greater than $P_2$ | Greater than $t_2$ |
| 16 | Equal to $T_2$ | Greater than $P_2$ | Less than $t_2$ |
| 17 | Equal to $T_2$ | Greater than $P_2$ | Equal to $t_2$ |
| 18 | Equal to $T_2$ | Less than $P_2$ | Greater than $t_2$ |
| 19 | Equal to $T_2$ | Equal to $P_2$ | Greater than $t_2$ |

Clearly, however, other possibilities are envisaged in which the conditions of the first step are less harsh than those of the second step, so in one such example (as outlined in the embodiments above) $T_1<T_2$; $P_1=P_2$; and $t_1=t_2$.

The one or more embodiments are described above by way of example only. Many variations are possible without departing from the scope of protection afforded by the appended claims.

The invention claimed is:

1. A method of forming an ostomy pouch; the method comprising:
   providing a film to form a first cavity wall and a second cavity wall;
   providing a comfort material to form a comfort layer; wherein the comfort material is a woven fabric material with a hot melt adhesive coating thereon;
   joining the first cavity wall to the second cavity wall at a first temperature and a first pressure for a first time period; and subsequently joining a comfort layer to at least one of the first and second cavity walls at a second temperature and a second pressure for a second time period;
   wherein the first temperature is less than the second temperature, the first pressure is about the same as that second pressure and the first time period is about equal to the second time period, thereby reducing the risk of damage to the comfort layer.

2. A method according to claim 1 wherein the join between the first cavity wall and second cavity wall overlaps the join between the comfort material and at least one of the first and second cavity walls.

3. A method according to claim 1, comprising providing a second comfort layer, wherein one of the comfort layers is joined concurrently with the joining of the first and second cavity walls.

4. A method according to claim 3 wherein the comfort layer joined concurrently with the joining of the first and second cavity walls is a body facing comfort layer.

5. A method according to claim 1, comprising providing a second comfort layer, wherein the two comfort layers are joined to the cavity walls concurrently.

6. A method according to claim 1 wherein the first and second cavity walls are joined by heat welding.

7. A method according to claim 1 wherein the one or more comfort layers are joined by heat activated adhesion.

8. A method according to claim 1 wherein the temperature and pressure are applied by at least one die.

9. A method according to claim 8 wherein temperature is applied by two dies on opposing sides of the join.

10. A method according to claim 9 wherein a different temperature is applied by each die.

11. A method according to claim 1, further comprising arranging the comfort layer with the hot melt adhesive adjacent to the cavity wall prior to joining, wherein a portion of the hot melt adhesive remains unbonded after the comfort layer is joined to the cavity wall.

12. A method according to claim 1, wherein the hot melt adhesive is a web comprising a mass and a plurality of voids in the mass.

13. A method according to claim 1 wherein the woven comfort material comprises polyester.

14. A method according to claim 1 wherein the hot-melt adhesive comprises ethylene-vinyl acetate (EVA).

15. A method according to claim 1 wherein the first temperature is between 100° C. and 150° C. and the second temperature is between 130° C. and 160° C.

16. A method according to claim 1 wherein the first pressure is between 2.5 bar and 2.7 bar and the second pressure is between 2.5 bar and 2.7 bar.

17. A method according to claim 1 wherein the first time period is between 500 ms and 750 ms and the second time period is between 500 ms and 750 ms.

18. A method according to claim 1, the further comprising applying the hot melt adhesive coating to the comfort material prior to joining the comfort material to at least one of the cavity walls.

19. A method according to claim 1, wherein the first temperature is greater than the second temperature and the first pressure is greater than the second pressure.

20. A method according to claim 19 wherein the first temperature is greater than the second temperature, the first pressure is greater than the second pressure and the first time period is equal to the second time period.

* * * * *